United States Patent
Jafari et al.

(10) Patent No.: US 9,498,202 B2
(45) Date of Patent: Nov. 22, 2016

(54) SUTURE SECUREMENT DEVICES

(71) Applicant: Edwards Lifesciences Corporation, Irvine, CA (US)

(72) Inventors: Mohammad Jafari, Foothill Ranch, CA (US); Ming H. Wu, Tustin, CA (US);

(Continued)

(73) Assignee: Edwards Lifesciences Corporation, Irvine, CA (US)

( * ) Notice: Subject to any disclaimer, the term of this patent is extended or adjusted under 35 U.S.C. 154(b) by 77 days.

(21) Appl. No.: 13/938,071

(22) Filed: Jul. 9, 2013

(65) Prior Publication Data
US 2014/0031864 A1 Jan. 30, 2014

Related U.S. Application Data

(60) Provisional application No. 61/720,886, filed on Oct. 31, 2012, provisional application No. 61/670,001, filed on Jul. 10, 2012.

(51) Int. Cl.
*A61B 17/04* (2006.01)
*A61B 17/064* (2006.01)
(Continued)

(52) U.S. Cl.
CPC ....... *A61B 17/0401* (2013.01); *A61B 17/0487* (2013.01); *A61B 17/0642* (2013.01);
(Continued)

(58) Field of Classification Search
CPC ............ A61B 17/0401; A61B 17/0642; A61B 2017/0488; A61B 2017/049; A61B
(Continued)

(56) References Cited

U.S. PATENT DOCUMENTS 1,358,477 A * 11/1920 Stout ..................... B65D 63/14
24/18
2,264,679 A 12/1941 Ravel
(Continued)

FOREIGN PATENT DOCUMENTS

CA 2141911 A1 8/1995
CA 2141913 A1 8/1995
(Continued)

OTHER PUBLICATIONS

International Search Report from Corresponding PCT Application No. PCT/US2013/049958, Mailed on Oct. 8, 2013.
(Continued)

*Primary Examiner* — Katrina Stransky
*Assistant Examiner* — Rachel S Highland
(74) *Attorney, Agent, or Firm* — Klarquist Sparkman, LLP

(57) ABSTRACT

Disclosed herein are exemplary embodiments of suture securement devices that replace the need to tie knots in sutures. Some embodiments comprise an annular outer body and one or more suture engagement tabs extending inwardly from the outer body. The devices can comprise a superelastic and/or shape-memory material and have a generally in-plane initial configuration. The suture engagement portions are deformable out-of-plane to an active configuration with the outer body compressed and the tabs interlocked with each other. The device can be heat-set in the deformed configuration. The interlocked tabs exert a pinching force on sutures passing between them that restricts the sutures from sliding through the opening in one longitudinal direction.

23 Claims, 29 Drawing Sheets

(72) Inventors: Hengchu Cao, Irvine, CA (US); Ralph Schneider, Irvine, CA (US); Manouchehr A. Miraki, Laguna Hills, CA (US)

(51) Int. Cl.
*A61F 2/08* (2006.01)
*B65D 33/16* (2006.01)
*A61F 2/24* (2006.01)

(52) U.S. Cl.
CPC .. *A61B 2017/042* (2013.01); *A61B 2017/0404* (2013.01); *A61B 2017/045* (2013.01); *A61B 2017/0406* (2013.01); *A61B 2017/049* (2013.01); *A61B 2017/0419* (2013.01); *A61B 2017/0437* (2013.01); *A61B 2017/0438* (2013.01); *A61B 2017/0446* (2013.01); *A61B 2017/0448* (2013.01); *A61B 2017/0451* (2013.01); *A61B 2017/0454* (2013.01); *A61B 2017/0456* (2013.01); *A61B 2017/0458* (2013.01); *A61B 2017/0461* (2013.01); *A61B 2017/0462* (2013.01); *A61B 2017/0464* (2013.01); *A61B 2017/0488* (2013.01); *A61F 2/0811* (2013.01); *A61F 2/2448* (2013.01); *B65D 33/1625* (2013.01); *Y10T 24/155* (2015.01); *Y10T 24/44923* (2015.01)

(58) Field of Classification Search
CPC ............... 2017/0404;A61B 2017/0406; A61B 2017/0419; A61B 2017/042; A61B 2017/0437; A61B 2017/0438; A61B 2017/0446; A61B 2017/0462; A61B 2017/0458; A61B 2017/0461; A61B 2017/0448; A61B 2017/045; A61F 2/0811; Y10T 24/155; Y10T 24/44923; B65D 33/1625
USPC ........................................................ 606/232
See application file for complete search history.

(56) References Cited

U.S. PATENT DOCUMENTS

| | | |
|---|---|---|
| 2,516,710 A | 7/1950 | Mascolo |
| 2,715,486 A | 8/1955 | Marcoff-Moghadam et al. |
| 2,890,519 A | 6/1959 | Storz, Jr. |
| 2,981,990 A * | 5/1961 | Balderree, Jr. .... B65D 33/1625 24/129 B |
| 3,143,742 A | 8/1964 | Cromie |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,541,591 A | 11/1970 | Hoegerman |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| RE27,391 E | 6/1972 | Merser |
| 3,753,438 A | 8/1973 | Wood et al. |
| 3,859,668 A | 1/1975 | Anderson |
| 3,875,648 A | 4/1975 | Bone |
| 3,898,999 A | 8/1975 | Haller |
| 3,910,281 A | 10/1975 | Kletschka et al. |
| 3,954,109 A | 5/1976 | Patel |
| 3,958,576 A | 5/1976 | Komiya |
| 3,976,079 A | 8/1976 | Samuels et al. |
| 3,988,810 A | 11/1976 | Emery |
| 3,996,623 A | 12/1976 | Kaster |
| 4,038,725 A | 8/1977 | Keefe |
| 4,103,690 A | 8/1978 | Harris |
| 4,140,125 A | 2/1979 | Smith |
| 4,170,990 A | 10/1979 | Baumgart et al. |
| 4,192,315 A | 3/1980 | Hilzinger et al. |
| 4,217,902 A | 8/1980 | March |
| 4,324,248 A | 4/1982 | Perlin |
| 4,345,601 A | 8/1982 | Fukuda |
| 4,416,266 A | 11/1983 | Baucom |
| 4,456,017 A | 6/1984 | Miles |
| 4,485,816 A | 12/1984 | Krumme |
| 4,522,207 A | 6/1985 | Klieman et al. |
| 4,535,764 A | 8/1985 | Ebert |
| 4,548,202 A | 10/1985 | Duncan |
| 4,549,545 A | 10/1985 | Levy |
| 4,570,304 A * | 2/1986 | Montreuil ......... B65D 33/1625 220/495.11 |
| 4,586,502 A | 5/1986 | Bedi et al. |
| 4,586,503 A | 5/1986 | Kirsch et al. |
| 4,595,007 A | 6/1986 | Mericle |
| 4,612,932 A | 9/1986 | Caspar et al. |
| 4,637,380 A | 1/1987 | Orejola |
| 4,665,906 A | 5/1987 | Jervis |
| 4,683,895 A | 8/1987 | Pohndorf |
| 4,705,040 A | 11/1987 | Mueller et al. |
| 4,719,924 A | 1/1988 | Crittenden et al. |
| 4,730,615 A | 3/1988 | Sutherland et al. |
| 4,741,330 A | 5/1988 | Hayhurst |
| 4,743,253 A | 5/1988 | Magladry |
| 4,750,492 A | 6/1988 | Jacobs |
| 4,809,695 A | 3/1989 | Gwathmey et al. |
| 4,823,794 A | 4/1989 | Pierce |
| 4,863,460 A | 9/1989 | Magladry |
| 4,873,975 A | 10/1989 | Walsh et al. |
| 4,896,668 A | 1/1990 | Popoff et al. |
| 4,899,744 A | 2/1990 | Fujitsuka et al. |
| 4,901,721 A | 2/1990 | Hakki |
| 4,914,789 A * | 4/1990 | Pedersen ............ B65D 33/1625 24/30.5 S |
| 4,924,866 A | 5/1990 | Yoon |
| 4,926,860 A | 5/1990 | Stice et al. |
| 4,929,240 A | 5/1990 | Kirsch et al. |
| 4,932,955 A | 6/1990 | Merz et al. |
| 4,950,283 A | 8/1990 | Dzubow et al. |
| 4,950,285 A | 8/1990 | Wilk |
| 4,955,913 A | 9/1990 | Robinson |
| 4,976,715 A | 12/1990 | Bays et al. |
| 4,983,176 A | 1/1991 | Cushman et al. |
| 4,990,152 A | 2/1991 | Yoon |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,026,379 A | 6/1991 | Yoon |
| 5,047,047 A | 9/1991 | Yoon |
| 5,053,047 A | 10/1991 | Yoon |
| 5,070,805 A | 12/1991 | Plante |
| 5,071,431 A | 12/1991 | Sauter et al. |
| 5,074,874 A | 12/1991 | Yoon et al. |
| 5,078,731 A | 1/1992 | Hayhurst |
| 5,100,418 A | 3/1992 | Yoon et al. |
| 5,116,840 A | 5/1992 | Ganguly et al. |
| 5,123,913 A | 6/1992 | Wilk et al. |
| RE34,021 E | 8/1992 | Mueller et al. |
| 5,152,769 A | 10/1992 | Baber |
| 5,154,189 A | 10/1992 | Oberlander |
| 5,158,566 A | 10/1992 | Pianetti |
| 5,163,954 A | 11/1992 | Curcio et al. |
| 5,171,250 A | 12/1992 | Yoon |
| 5,171,251 A | 12/1992 | Bregen et al. |
| 5,171,252 A | 12/1992 | Friedland |
| 5,174,087 A | 12/1992 | Bruno |
| 5,196,022 A | 3/1993 | Bilweis |
| 5,219,358 A | 6/1993 | Bendel et al. |
| 5,222,976 A | 6/1993 | Yoon |
| 5,231,735 A * | 8/1993 | Paxton ............... B65D 33/1625 24/30.5 S |
| 5,234,449 A | 8/1993 | Bruker et al. |
| 5,236,440 A | 8/1993 | Hlavacek |
| 5,242,456 A | 9/1993 | Nash et al. |
| 5,246,443 A | 9/1993 | Mai |
| 5,258,011 A | 11/1993 | Drews |

(56) References Cited

U.S. PATENT DOCUMENTS

| | | |
|---|---|---|
| 5,258,015 A | 11/1993 | Li et al. |
| 5,269,783 A | 12/1993 | Sander |
| 5,269,809 A | 12/1993 | Hayhurst et al. |
| 5,282,832 A | 2/1994 | Toso et al. |
| 5,290,289 A | 3/1994 | Sanders et al. |
| 5,304,204 A | 4/1994 | Bregen |
| 5,306,290 A | 4/1994 | Martins et al. |
| 5,306,296 A | 4/1994 | Wright et al. |
| 5,312,436 A | 5/1994 | Coffey et al. |
| 5,330,503 A | 7/1994 | Yoon |
| 5,336,239 A | 8/1994 | Gimpelson |
| 5,356,424 A | 10/1994 | Buzerak et al. |
| 5,374,268 A | 12/1994 | Sander |
| 5,381,588 A * | 1/1995 | Nelson .............. B65D 73/0064 24/30.5 S |
| 5,383,904 A | 1/1995 | Totakura et al. |
| 5,383,905 A | 1/1995 | Golds et al. |
| 5,391,173 A | 2/1995 | Wilk |
| 5,403,346 A | 4/1995 | Loeser |
| 5,409,499 A | 4/1995 | Yi |
| 5,437,680 A | 8/1995 | Yoon |
| 5,437,685 A | 8/1995 | Blasnik |
| 5,439,479 A | 8/1995 | Shichman et al. |
| 5,445,167 A | 8/1995 | Yoon et al. |
| 5,450,860 A | 9/1995 | O'Connor |
| 5,452,733 A | 9/1995 | Sterman et al. |
| 5,456,246 A | 10/1995 | Schmieding et al. |
| 5,462,561 A | 10/1995 | Voda |
| 5,474,557 A | 12/1995 | Mai |
| 5,474,572 A | 12/1995 | Hayhurst |
| 5,480,405 A | 1/1996 | Yoon |
| 5,486,197 A | 1/1996 | Le et al. |
| 5,496,336 A | 3/1996 | Cosgrove et al. |
| 5,499,990 A | 3/1996 | Schulken et al. |
| 5,500,000 A | 3/1996 | Feagin et al. |
| 5,520,691 A | 5/1996 | Branch |
| 5,520,702 A | 5/1996 | Sauer et al. |
| 5,527,342 A | 6/1996 | Pietrzak et al. |
| 5,531,763 A | 7/1996 | Mastri et al. |
| 5,545,178 A | 8/1996 | Kensey et al. |
| 5,549,619 A | 8/1996 | Peters et al. |
| 5,562,685 A | 10/1996 | Mollenauer et al. |
| 5,569,274 A | 10/1996 | Rapacki et al. |
| 5,569,301 A | 10/1996 | Granger et al. |
| 5,582,616 A | 12/1996 | Bolduc et al. |
| 5,582,619 A | 12/1996 | Ken |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup, III |
| 5,609,608 A | 3/1997 | Benett et al. |
| 5,626,590 A | 5/1997 | Wilk |
| 5,630,824 A | 5/1997 | Hart |
| 5,632,752 A | 5/1997 | Buelna |
| 5,632,753 A | 5/1997 | Loeser |
| 5,643,289 A | 7/1997 | Sauer et al. |
| 5,643,295 A | 7/1997 | Yoon |
| 5,645,553 A | 7/1997 | Kolesa et al. |
| 5,645,568 A | 7/1997 | Chervitz et al. |
| 5,665,109 A | 9/1997 | Yoon |
| 5,669,917 A | 9/1997 | Sauer et al. |
| 5,669,935 A | 9/1997 | Rosenman et al. |
| 5,681,351 A | 10/1997 | Jamiolkowski et al. |
| 5,683,417 A | 11/1997 | Cooper |
| 5,695,505 A | 12/1997 | Yoon |
| 5,697,943 A | 12/1997 | Sauer et al. |
| 5,700,270 A | 12/1997 | Peyser et al. |
| 5,700,271 A | 12/1997 | Whitfield et al. |
| 5,707,380 A | 1/1998 | Hinchliffe et al. |
| 5,709,693 A | 1/1998 | Taylor |
| 5,709,695 A | 1/1998 | Northrup, III |
| 5,725,539 A | 3/1998 | Matern |
| 5,725,542 A | 3/1998 | Yoon |
| 5,725,556 A | 3/1998 | Moser et al. |
| 5,728,135 A | 3/1998 | Bregen et al. |
| 5,735,290 A | 4/1998 | Sterman et al. |
| 5,735,877 A | 4/1998 | Pagedas |
| 5,766,183 A | 6/1998 | Sauer |
| 5,776,188 A | 7/1998 | Shepherd et al. |
| 5,799,661 A | 9/1998 | Boyd et al. |
| 5,810,851 A | 9/1998 | Yoon |
| 5,810,882 A | 9/1998 | Bolduc et al. |
| 5,820,631 A | 10/1998 | Nobles |
| 5,824,008 A | 10/1998 | Bolduc et al. |
| 5,830,221 A | 11/1998 | Stein et al. |
| 5,833,696 A | 11/1998 | Whitfield et al. |
| 5,845,645 A | 12/1998 | Bonutti |
| 5,849,019 A | 12/1998 | Yoon |
| 5,852,851 A * | 12/1998 | Cooper .............. B65D 33/1625 24/30.5 R |
| 5,861,004 A | 1/1999 | Kensey et al. |
| 5,879,371 A | 3/1999 | Gardiner et al. |
| 5,891,130 A | 4/1999 | Palermo et al. |
| 5,891,160 A | 4/1999 | Williamson, IV et al. |
| 5,895,393 A | 4/1999 | Pagedas |
| 5,895,394 A | 4/1999 | Kienzle et al. |
| 5,919,207 A | 7/1999 | Taheri |
| 5,948,001 A | 9/1999 | Larsen |
| 5,961,481 A | 10/1999 | Sterman et al. |
| 5,961,539 A | 10/1999 | Northrup, III et al. |
| 5,964,772 A | 10/1999 | Bolduc et al. |
| 5,972,024 A | 10/1999 | Northrup, III et al. |
| 5,976,159 A | 11/1999 | Bolduc et al. |
| 5,984,917 A | 11/1999 | Fleischman et al. |
| 5,989,242 A | 11/1999 | Saadat et al. |
| 5,989,268 A | 11/1999 | Pugsley, Jr. et al. |
| 5,997,556 A | 12/1999 | Tanner |
| 6,001,110 A | 12/1999 | Adams |
| 6,013,084 A | 1/2000 | Ken et al. |
| 6,015,428 A | 1/2000 | Pagedas |
| 6,039,176 A | 3/2000 | Wright |
| 6,066,160 A | 5/2000 | Colvin et al. |
| 6,074,409 A | 6/2000 | Goldfarb |
| 6,120,524 A | 9/2000 | Taheri |
| 6,132,438 A | 10/2000 | Fleischman et al. |
| 6,139,540 A | 10/2000 | Rost et al. |
| 6,143,004 A | 11/2000 | Davis et al. |
| 6,176,413 B1 | 1/2001 | Heck et al. |
| 6,190,373 B1 | 2/2001 | Palermo et al. |
| 6,193,733 B1 | 2/2001 | Adams |
| 6,193,734 B1 | 2/2001 | Bolduc et al. |
| 6,231,592 B1 | 5/2001 | Bonutti et al. |
| 6,241,765 B1 | 6/2001 | Griffin et al. |
| 6,254,615 B1 | 7/2001 | Bolduc et al. |
| 6,306,141 B1 | 10/2001 | Jervis |
| 6,346,112 B2 | 2/2002 | Adams |
| 6,368,334 B1 | 4/2002 | Sauer |
| 6,432,123 B2 | 8/2002 | Schwartz et al. |
| 6,475,230 B1 | 11/2002 | Bonutti et al. |
| 6,514,265 B2 | 2/2003 | Ho et al. |
| 6,533,796 B1 | 3/2003 | Sauer et al. |
| 6,537,290 B2 | 3/2003 | Adams et al. |
| 6,551,332 B1 | 4/2003 | Nguyen et al. |
| 6,589,279 B1 | 7/2003 | Anderson et al. |
| 6,607,541 B1 | 8/2003 | Gardiner et al. |
| 6,613,059 B2 | 9/2003 | Schaller et al. |
| 6,626,930 B1 | 9/2003 | Allen et al. |
| 6,641,592 B1 | 11/2003 | Sauer et al. |
| 6,641,593 B1 | 11/2003 | Schaller et al. |
| 6,682,540 B1 | 1/2004 | Sancoff et al. |
| 6,719,767 B1 | 4/2004 | Kimblad |
| 6,746,457 B2 | 6/2004 | Dana et al. |
| 6,749,622 B2 | 6/2004 | McGuckin, Jr. et al. |
| 6,776,784 B2 | 8/2004 | Ginn |
| 6,860,890 B2 | 3/2005 | Bachman et al. |
| 6,896,686 B2 | 5/2005 | Weber |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,945,980 B2 | 9/2005 | Nguyen et al. |
| 6,960,221 B2 | 11/2005 | Ho et al. |
| 7,011,669 B2 | 3/2006 | Kimblad |
| 7,083,628 B2 | 8/2006 | Bachman |

(56) References Cited

U.S. PATENT DOCUMENTS

| | | |
|---|---|---|
| 7,094,244 B2 | 8/2006 | Schreck |
| 7,112,207 B2 | 9/2006 | Allen et al. |
| 7,220,266 B2 | 5/2007 | Gambale |
| 7,235,086 B2 | 6/2007 | Sauer et al. |
| 7,264,625 B1 | 9/2007 | Buncke |
| 7,381,210 B2 | 6/2008 | Zarbatany et al. |
| 7,628,797 B2 | 12/2009 | Tieu et al. |
| 7,677,525 B2* | 3/2010 | Sanchez ............... A01G 9/128 24/30.5 S |
| 7,731,727 B2 | 6/2010 | Sauer |
| 7,833,237 B2 | 11/2010 | Sauer |
| 7,842,051 B2 | 11/2010 | Dana et al. |
| 7,862,584 B2 | 1/2011 | Lyons et al. |
| 7,875,056 B2 | 1/2011 | Jervis et al. |
| 7,959,674 B2 | 6/2011 | Shu et al. |
| 7,981,139 B2 | 7/2011 | Martin et al. |
| 8,021,421 B2 | 9/2011 | Fogarty et al. |
| 8,100,923 B2 | 1/2012 | Paraschac et al. |
| 8,105,355 B2 | 1/2012 | Page et al. |
| 8,252,005 B2 | 8/2012 | Findlay, III et al. |
| 8,398,657 B2 | 3/2013 | Sauer |
| 8,398,680 B2 | 3/2013 | Sauer et al. |
| 8,425,555 B2 | 4/2013 | Page et al. |
| 8,480,686 B2 | 7/2013 | Bakos et al. |
| 8,753,373 B2 | 6/2014 | Chau et al. |
| 9,017,347 B2 | 4/2015 | Oba et al. |
| 2001/0025181 A1* | 9/2001 | Freedlan .................... 606/73 |
| 2003/0109922 A1 | 6/2003 | Peterson et al. |
| 2003/0195563 A1 | 10/2003 | Foerster |
| 2003/0233105 A1 | 12/2003 | Gayton |
| 2004/0181238 A1 | 9/2004 | Zarbatany et al. |
| 2004/0204724 A1* | 10/2004 | Kissel ............... A61B 17/0487 606/151 |
| 2004/0249414 A1 | 12/2004 | Kissel et al. |
| 2005/0251206 A1* | 11/2005 | Maahs ............... A61B 17/0401 606/232 |
| 2005/0251209 A1 | 11/2005 | Saadat et al. |
| 2006/0047314 A1 | 3/2006 | Green |
| 2006/0079913 A1 | 4/2006 | Whitfield et al. |
| 2006/0089571 A1 | 4/2006 | Gertner |
| 2006/0184203 A1 | 8/2006 | Martin et al. |
| 2006/0265010 A1 | 11/2006 | Paraschac et al. |
| 2006/0276871 A1 | 12/2006 | Lamson et al. |
| 2006/0282119 A1* | 12/2006 | Perchik ............... A61B 17/0401 606/232 |
| 2007/0005079 A1 | 1/2007 | Zarbatany et al. |
| 2007/0005081 A1 | 1/2007 | Findlay et al. |
| 2007/0049952 A1 | 3/2007 | Weiss |
| 2007/0049970 A1 | 3/2007 | Belef et al. |
| 2007/0088391 A1 | 4/2007 | McAlexander et al. |
| 2007/0179530 A1 | 8/2007 | Tieu et al. |
| 2007/0270907 A1 | 11/2007 | Stokes et al. |
| 2008/0154286 A1 | 6/2008 | Abbott et al. |
| 2008/0255591 A1 | 10/2008 | Harada et al. |
| 2008/0281356 A1 | 11/2008 | Chau et al. |
| 2009/0143821 A1 | 6/2009 | Stupak |
| 2009/0281377 A1* | 11/2009 | Newell ............... A61B 17/0469 600/104 |
| 2009/0281568 A1* | 11/2009 | Cendan ............... A61B 17/0401 606/217 |
| 2010/0001038 A1 | 1/2010 | Levin et al. |
| 2010/0076462 A1 | 3/2010 | Bakos et al. |
| 2010/0324597 A1 | 12/2010 | Shikhman |
| 2011/0087241 A1 | 4/2011 | Nguyen |
| 2011/0087242 A1 | 4/2011 | Pribanic et al. |
| 2011/0224714 A1 | 9/2011 | Gertner |
| 2011/0283514 A1 | 11/2011 | Fogarty et al. |
| 2012/0089182 A1 | 4/2012 | Page et al. |
| 2012/0101526 A1* | 4/2012 | Bennett ...................... 606/232 |
| 2012/0102526 A1 | 4/2012 | Lejeune |
| 2013/0053884 A1 | 2/2013 | Roorda |
| 2013/0110164 A1 | 5/2013 | Milazzo et al. |
| 2013/0158600 A1 | 6/2013 | Conklin et al. |
| 2013/0282028 A1 | 10/2013 | Conklin et al. |
| 2014/0031864 A1 | 1/2014 | Jafari et al. |

FOREIGN PATENT DOCUMENTS

| | | |
|---|---|---|
| CN | 2558335 Y | 7/2003 |
| DE | 69512446 T2 | 5/2000 |
| DE | 69612447 T2 | 7/2001 |
| EP | 0669101 A1 | 8/1995 |
| EP | 0669103 A1 | 8/1995 |
| EP | 1484023 A1 | 12/2004 |
| WO | 0149207 A2 | 7/2001 |
| WO | 0166001 A2 | 9/2001 |

OTHER PUBLICATIONS

European Search Report issued for Application No. 12858766.4, Sep. 16, 2015.
International Search Report for PCT/US2014/046423, Oct. 20, 2014.
EP Supplementary Search Report for EP12858766, completed Sep. 7, 2015.
CN Office Action for App No. 2012800690769, Mar. 23, 2015.
European Supplementary Search Report issued Feb. 9, 2016 for EP13817447.
Office Action and Search Report issued in CN Application No. 2013800370373, Mar. 28, 2016.
Int'l. Search Report for PCT/US15/065033, mailed Feb. 18, 2016.
Int'l. Search Report for PCT/US2016/022495, mailed Jun. 1, 2016.

* cited by examiner

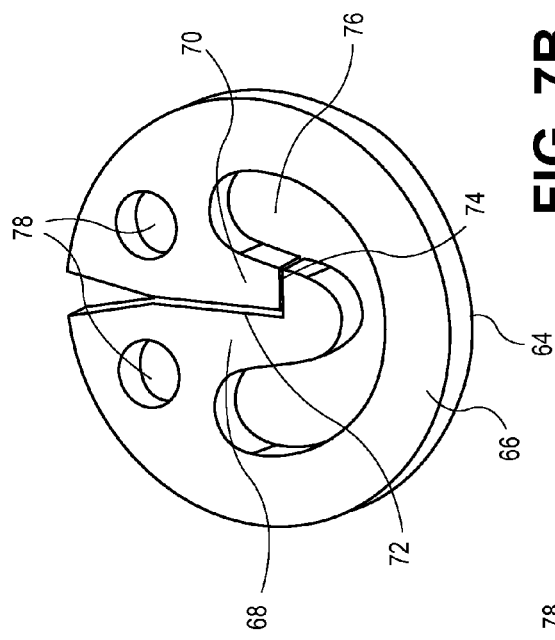
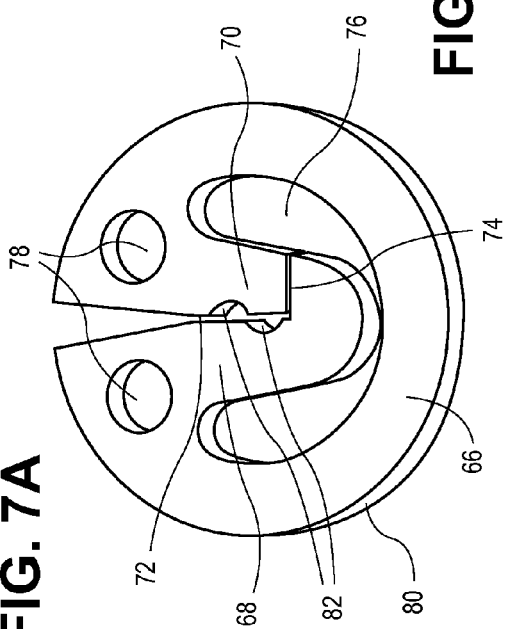
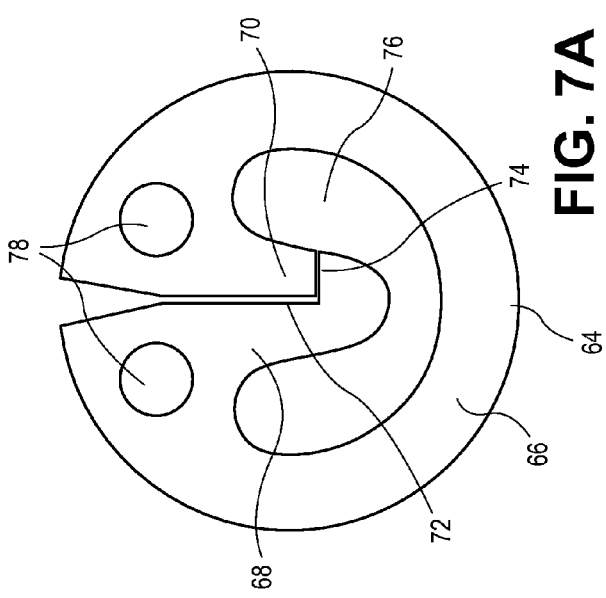
FIG. 7A
FIG. 7B
FIG. 8

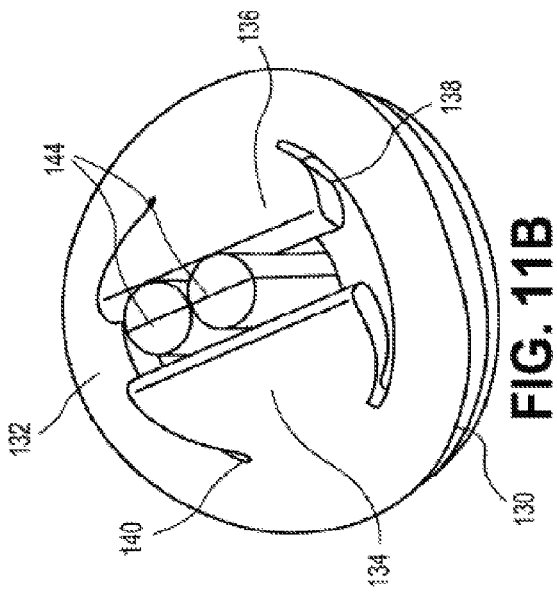
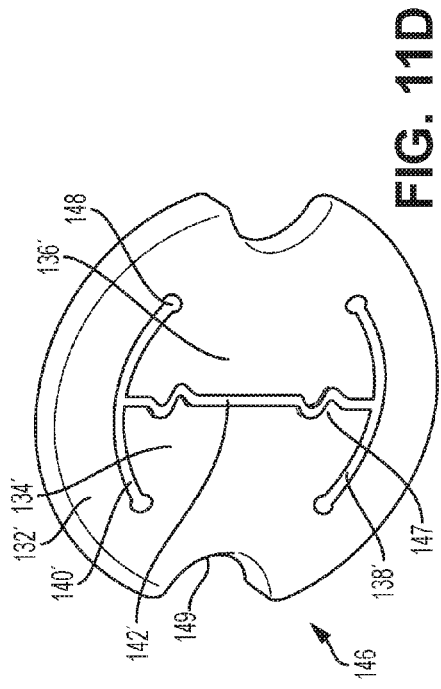
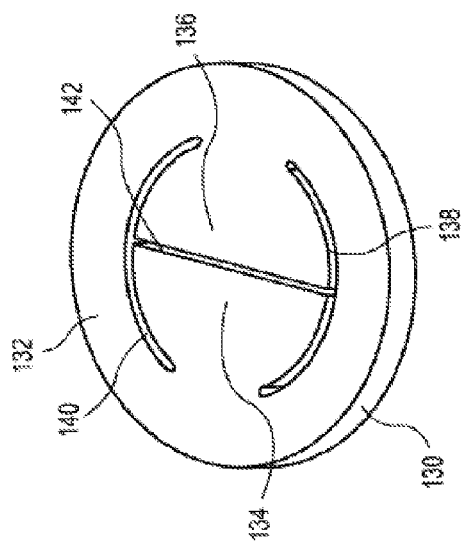
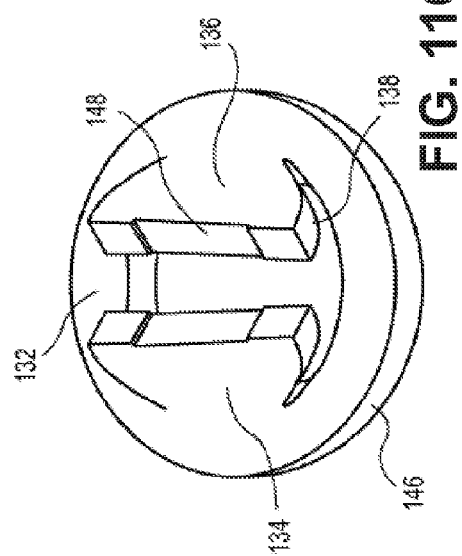

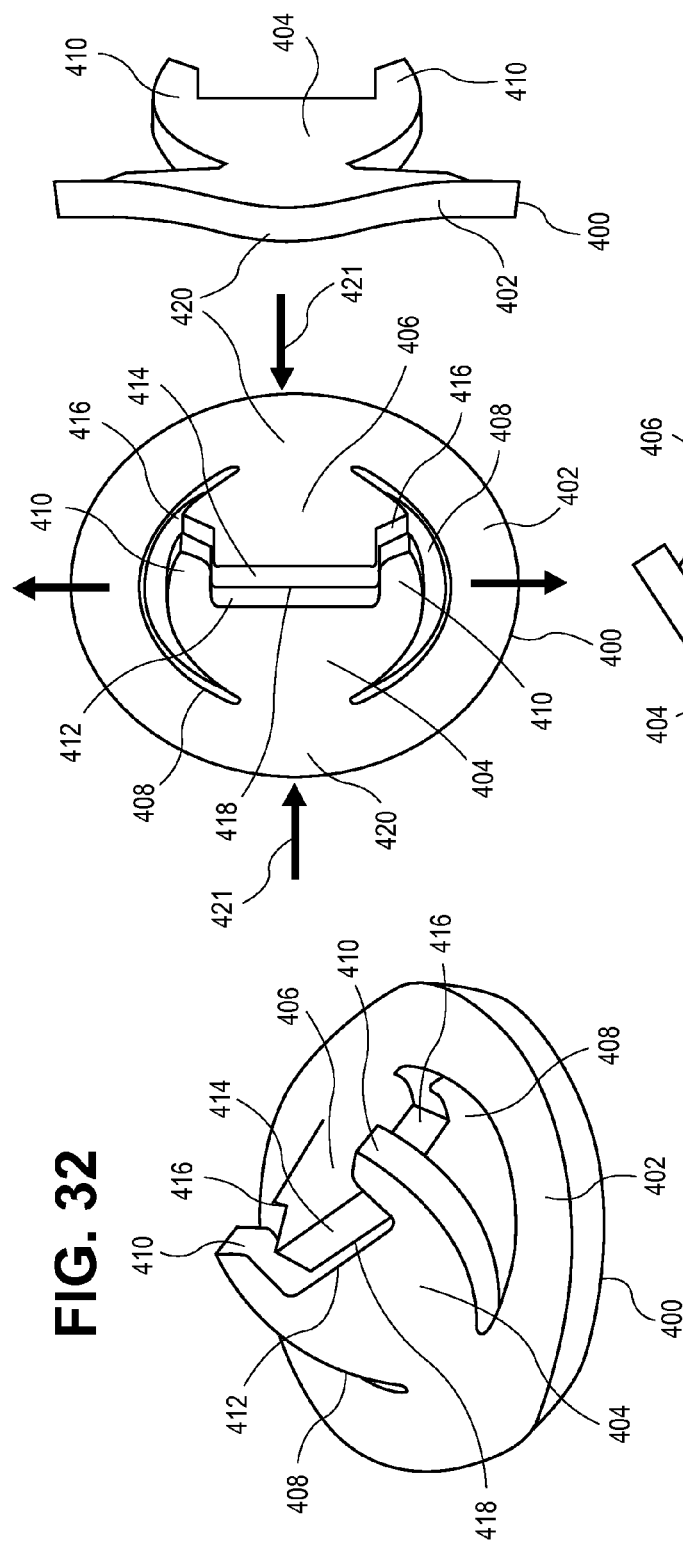

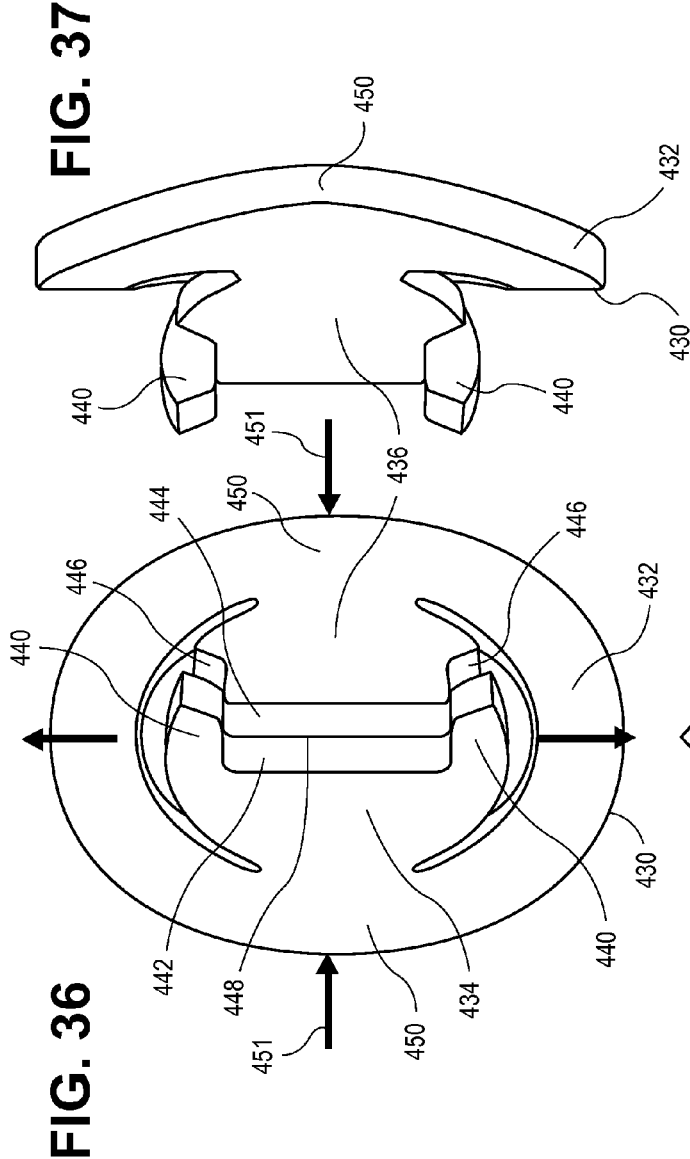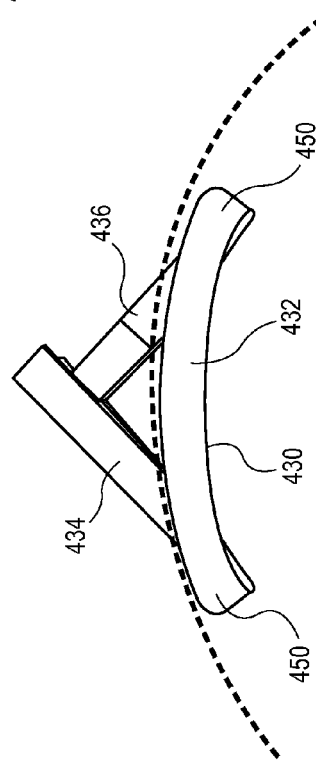

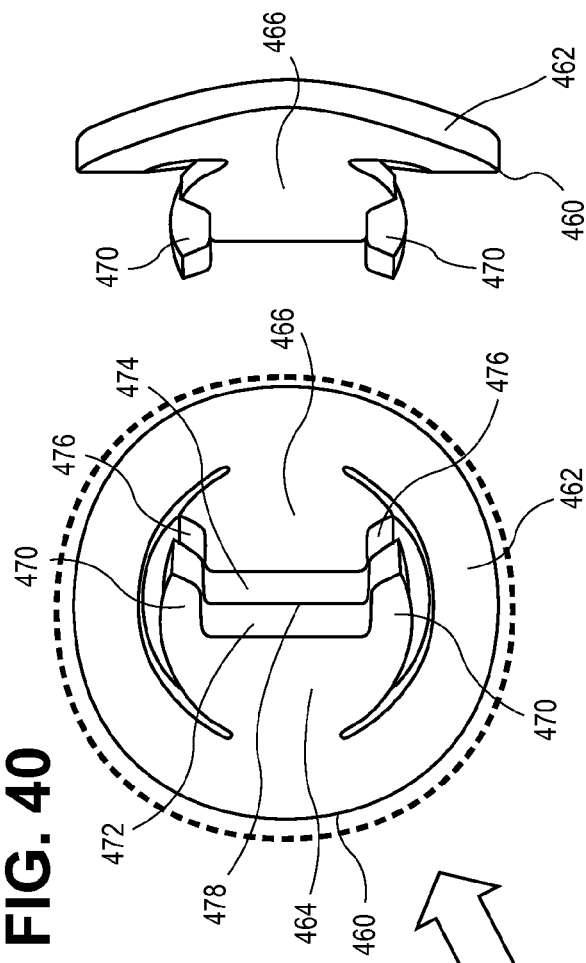
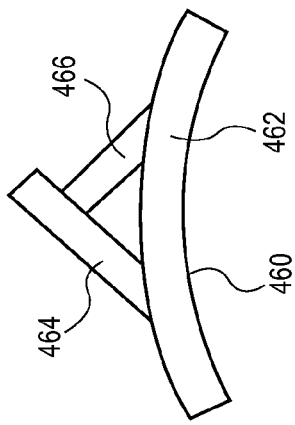
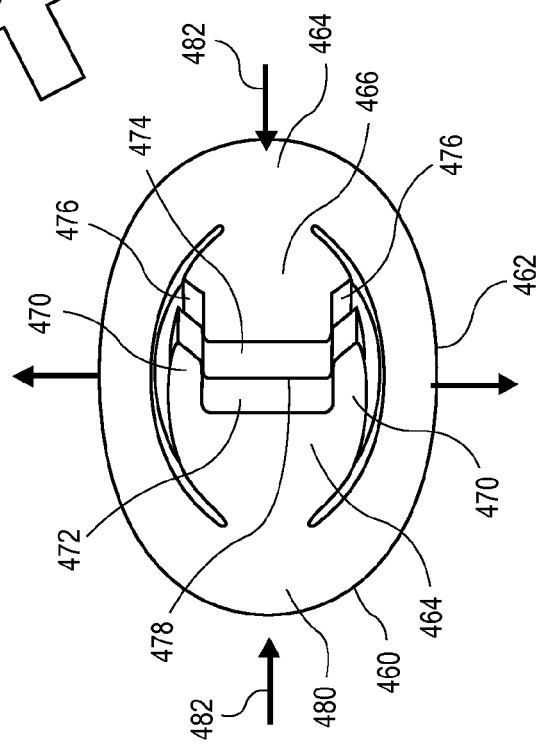

SUTURE SECUREMENT DEVICES

RELATED APPLICATIONS

This application claims priority under 35 U.S.C. §119 to U.S. Provisional Application No. 61/720,886, filed Oct. 31, 2012, and to U.S. Provisional Application No. 61/670,001, filed Jul. 10, 2012.

FIELD

This disclosure relates to devices for securing sutures.

BACKGROUND

Prosthetic devices are often implanted using sutures. For example, prosthetic heart valves and annuloplasty rings can be secured to a native valve annulus using sutures. Conventionally, the loose ends of the sutures are tied in knots to secure them together and/or to secure the prosthetic device to the adjacent tissue. However, the process of tying knots in sutures can be time consuming and difficult, the amount of slack left in the sutures can be difficult to control, the knots can be difficult or impossible to untie, and/or the knots can accidentally come loose. Thus, there is a need in the art for ways to secure sutures without tying knots.

SUMMARY

Disclosed herein are exemplary embodiments of suture securement devices that replace the need to tie knots in sutures. Some embodiments of a suture securement device comprise an outer body, an opening passing through the outer body for receiving one or more sutures, and at least one suture engagement portion extending from the outer body to the opening. The device comprises a resiliently deformable material and has a natural configuration when no sutures are positioned in the opening. The opening has a width that is smaller than a diameter of the suture when the device is in the natural configuration. The at least one suture engagement portion is resiliently deformable to an active configuration when a suture is positioned through the opening. In the active configuration, the at least one suture engagement portion exerts a pinching force on the suture that restricts the suture from sliding through the opening in at least one longitudinal direction of the suture.

In some of these embodiments, the device comprises two, three, four, or more suture engagement portions extending inwardly from the outer body that are resiliently deformable to an active configuration when one or more sutures are positioned through the opening.

In some embodiments, the outer body comprises a fully annular body that encloses the opening, while in other embodiments, the outer body comprises a radial slit or opening that communicates with the opening to allow a suture to be slid laterally through the slit into the opening. In some of the embodiments with a slit, the device further comprises an open region between a portion of the outer body and the suture engagement portions, and the open region communicates with the opening and the slit.

In some embodiments, at least one of the suture engagement portions projects out-of-plane from the outer body in the natural configuration, such that the device is biased to allow a suture positioned in the opening to slide through the opening with relatively little resistance in one longitudinal direction while preventing the suture from sliding through the opening in the other longitudinal direction.

Some exemplary devices for securing one or more sutures comprising a first end portion, a second end portion, and an intermediate third portion coupling the first end portion to the second end portion. Each of the first, second and third portions comprise an at least partially annular body having an internal passageway extending therethrough in a longitudinal direction of the device. The first, second and third portions are resiliently deformable relative to one another in a plane generally perpendicular to the longitudinal direction. The device has a natural configuration, free of elastic deformation, wherein at least one of the first, second and third portions is twisted relative to the other portions such that the internal passageways are misaligned with one another; and the device has a deformed configuration wherein at least one of the first, second and third portions is resiliently deformed relative the other portions such that the internal passageways of the first, second and third portions are substantially aligned in the longitudinal direction. One or more sutures can be positioned through the aligned internal passageways when the device is in the deformed configuration and the device is configured to pinch the one or more sutures between the first, second and third portions when the device is allowed to return toward its natural configuration.

Some embodiments comprise a first spine segment flexibly coupling the first end portion to the third portion and a second spine segment flexibly coupling the second end portion to the third portion. Each of the first, second and third portions can comprise a partially annular body having an open section, wherein the open sections of the first, second and third portions are misaligned in the natural configuration and are aligned in the deformed configuration to allow one or more sutures to be laterally inserted into the internal passageways. The first and second end portions can be aligned with each other in the longitudinal direction in both the natural and deformed configurations.

In some implementations, a tool can be used with the device to hold the device in the deformed configuration and then release the device to return toward the natural configuration. The tool can comprise a handle and first and second jaws that are configured to apply a compression force on the device to hold it in the deformed position while one or more sutures are inserted laterally through the aligned open sections.

Some embodiments of suture securement devices described herein can have a curved body that has a generally uniform thickness and/or generally parallel convex and concave major surfaces. In some embodiments, the curved devices can be cut from a sidewall of a tube, such as tube having a circular cross-sectional profile and a uniform wall thickness. The curved devices can be biased such that suture(s) can be readily inserted through the device from the concave side and are prevented from sliding back out through the concave side.

An exemplary method of forming a suture clip can comprise first forming a flat or curved suture clip having an annular outer body and an a two opposing tabs extending toward each other within the outer body, with the tabs being in-plane with the outer body. For instance, curved slots on either side of the tabs and a middle slit between the tabs connect to each other but do not intersect with an outer edge of the body, thus forming a "closed" generally H-shaped opening extending from one face of the device to the other. The method can further comprise bending the suture clip to a deformed configuration with the outer body compressed in an in-plane direction and the tabs extending out-of-plane from the outer body. The method can further comprise heat-setting the suture clip in the deformed configuration.

The clip can comprise a superelastic and/or shape-memory material such as Nitinol. In some embodiments, the two tabs interlock with each other in the deformed configuration. In some embodiments, the outer body is compressed in the direction that the tabs extend from the outer body. In some embodiments, bending the suture clip comprises compressing the outer body from a generally elliptical shape to a generally circular shape, or from a generally circular shape to a generally elliptical shape.

Some exemplary suture clips comprising an upper panel and a lower panel coupled together along a fold line at one end. The upper panel can comprise a slit and a biased tab configured to allow a suture engaged in the slit to slide more freely in one axial direction and less freely in an opposite axial direction, and the lower panel can comprise a slot configured to constrain a sutured engaged in the slit from migrating along the length of the slit.

The foregoing and other objects, features, and advantages of the invention will become more apparent from the following detailed description, which proceeds with reference to the accompanying figures.

BRIEF DESCRIPTION OF THE DRAWINGS

FIG. 7A is a plan view of another exemplary suture clip.

FIG. 7B is a perspective view of the suture clip of FIG. 7A.

FIG. 8 is a perspective view of another exemplary suture clip.

FIG. 11A is a perspective view of another exemplary suture clip.

FIG. 11B is another perspective view of the suture clip of FIG. 11A, showing the clip engaged with two sutures.

FIG. 11C is a perspective view of another exemplary suture clip.

FIG. 11D is a perspective view of another exemplary suture clip having serpentine sections of a central slit to help retain sutures therein.

FIGS. 32-35 are various views of another exemplary suture clip.

FIGS. 36-38 are various views of yet another exemplary suture clip.

FIGS. 39-42 are various views of still another exemplary suture clip.

DETAILED DESCRIPTION

Rather than tying knots to secure sutures, suture clips or other suture securement devices can be placed on sutures to secure them. Several exemplary embodiments of suture securement devices are disclosed herein and shown in the attached figures. These embodiments should not be construed as limiting in any way. Instead, the present disclosure is directed toward all novel and nonobvious features and aspects of the various disclosed embodiments, alone and in various combinations and sub-combinations with one another.

The disclosed devices can secure a single suture or to two or more sutures at the same time. For ease of description, this disclosure generally describes the various embodiments in use with only a single suture, though it should be understood that the disclosed embodiments may be used with two or more sutures in the same or similar manner, unless otherwise described.

The disclosed devices can be positioned on a suture by threading a free end of the suture through an opening in the device and/or by sliding the suture laterally through a slit in the side of the device, depending on the particular embodiment. For example, the embodiment shown in FIGS. 3 and 4 require that an end of a suture be threaded through an enclosed opening in the device, whereas the embodiments of FIGS. 5-10 also have a slit in a lateral side that allows an intermediate portion of a suture to be laterally inserted into the device.

Once a suture securement device is positioned on a suture, the device can prevent the suture from sliding axially through the device in one or both longitudinal directions of the suture. In some embodiments, the device can be biased to allow the suture to slide through the device in one longitudinal direction, but prevent the suture from sliding in the opposite direction, forming a one-way suture lock, or ratchet mechanism. In other embodiments, the device can prevent the suture from sliding in both longitudinal directions, forming a more restrictive two-way suture lock.

Figure 1:
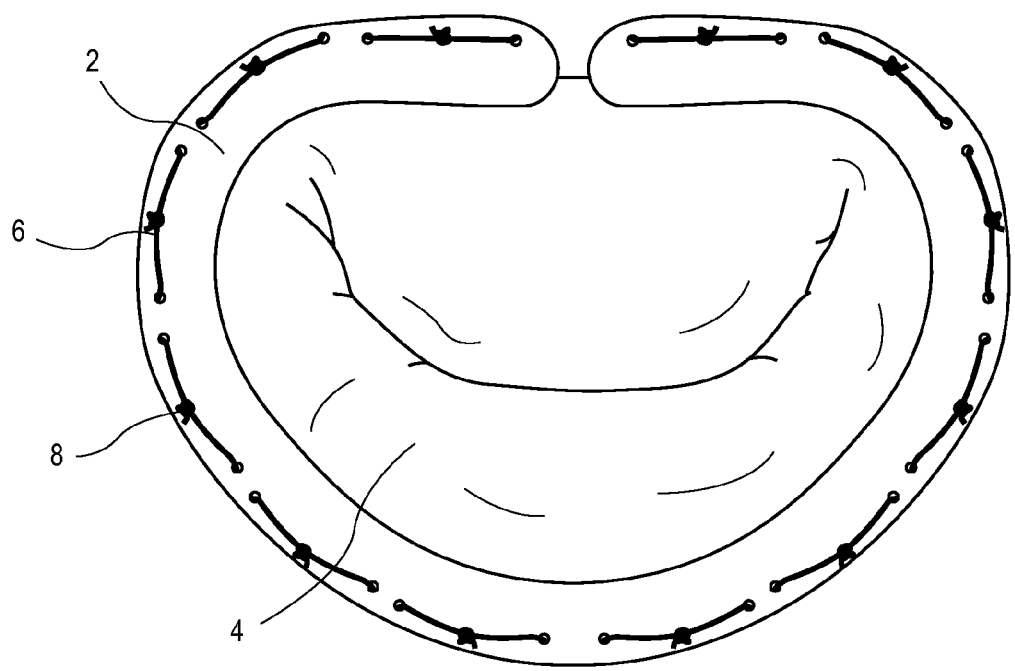
FIG. 1 is a top view of an exemplary annuloplasty ring implanted at the mitral annulus using knotted sutures.
Figure 2:
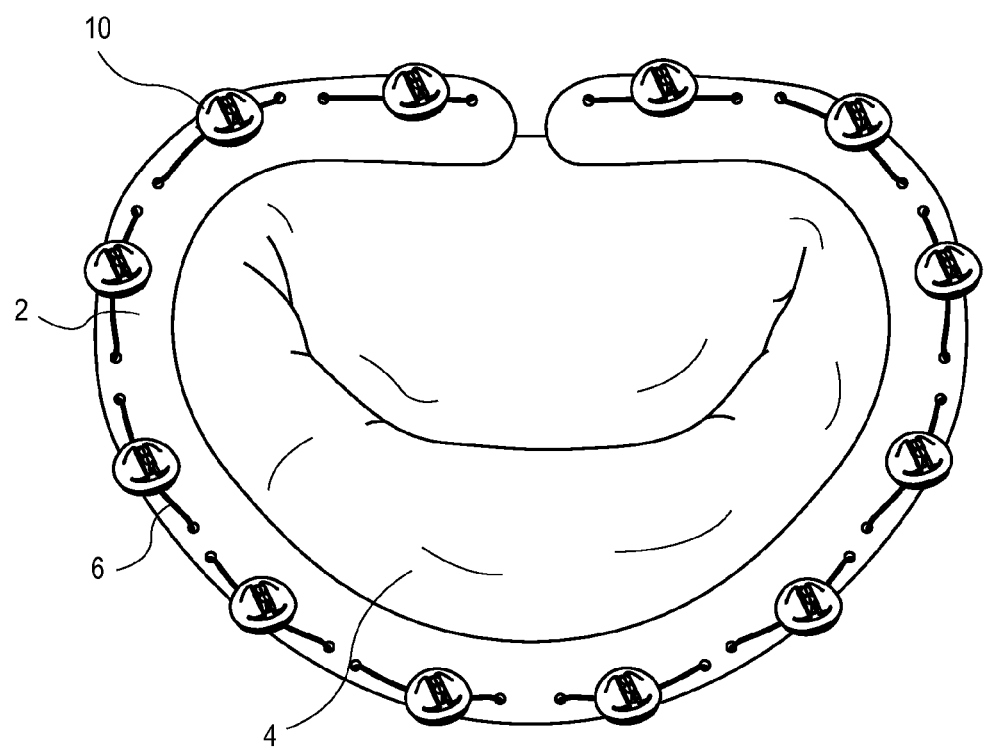
FIG. 2 is a top view of an exemplary annuloplasty ring implanted at the mitral annulus using exemplary suture clips to secure the sutures.

FIG. 1 shows an exemplary prosthetic device in the form of an annuloplasty ring 2 secured to the annulus of a native mitral valve 4 using sutures 6. Ends of the sutures 6 are secured together using conventional knots 8. FIG. 2 shows the same annuloplasty ring 2 secured to the mitral annulus using exemplary suture securement devices 10 instead of knots. Twelve devices 10 are used in this example, though different numbers of devices can be used in other implementations. In this example, each device 10 secures together two sutures 6 extending from opposite directions, in place of a standard knot. In other examples, a separate device 10 can be secured to each suture 6 at the location where the suture passes through the annuloplasty ring 2. Either way, the devices 10 prevent the sutures 6 from sliding through the devices toward the annuloplasty ring 2, keeping the sutures taught and keeping the ring 2 secured against the mitral valve tissue 4. In some embodiments, such as the devices 10 shown in FIG. 2, the devices also allow the sutures 6 to be further tightened after an initial deployment to reduce any excess slack in the sutures. Though the exemplary suture securement devices 10 are shown in the example of FIG. 2, any of the embodiments disclosed herein can be used for the same or similar purposes on other implementations.

While FIG. 2 shows an annuloplasty ring being secured by devices 10, the devices 10, as well as the other embodiments of suture securement devices disclosed herein, can be used to secure other prosthetic devices to tissue in the body. Other prosthetic devices include, for example, prosthetic heart valves, stents, grafts, and various other prosthetic implants conventionally secured to tissue using sutures.

By using the disclosed suture securement devices rather than tying knots in the sutures, the sutures can be secured in less time and with less difficulty (especially in hard-to-reach locations). In addition, some suture securement devices can allow the amount of slack left in the sutures to be more precisely controlled, the devices can be less likely to come loose than knots, and some embodiments of the devices can be easily removed or adjusted after they are initially deployed. Furthermore, the suture securement devices can be small, durable, biocompatible, and inexpensive.

Figure 3:
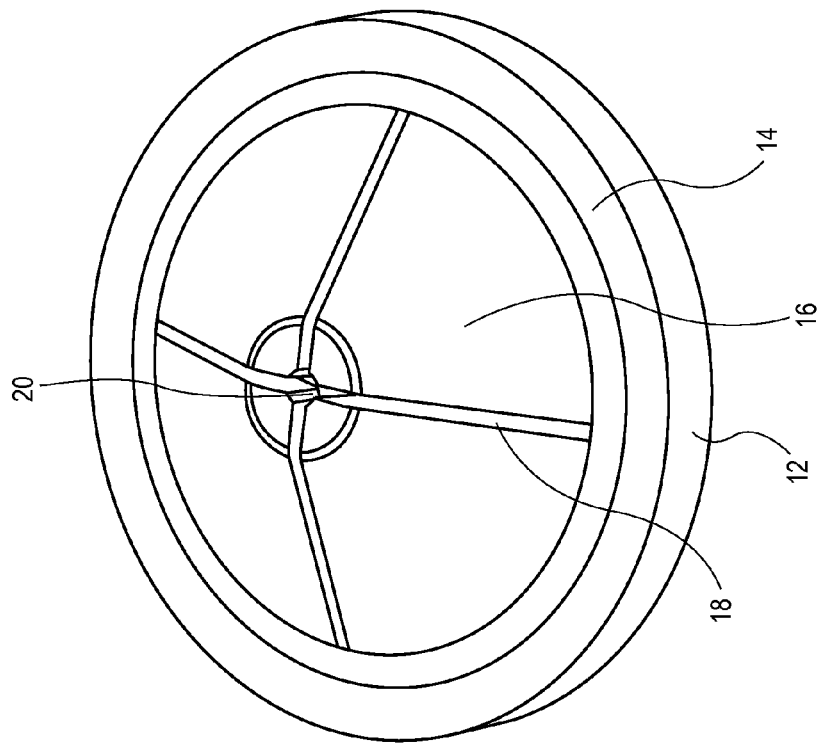
FIG. 3 is a perspective view of an exemplary suture clip.

FIG. 3 shows an exemplary embodiment of an enclosed, biased suture securement device 12. The device 12 comprises an annular outer body 14 and four triangular tabs 16 that extend out-of-plane from the outer body 14. The tabs 16 are separated by four radial slits 18 extending from a central opening 20. Because there are no lateral slits in the outer body 14 (i.e., the device 12 is "enclosed"), an end of a suture is threaded through the opening 20 to engage the device 12 with the suture. Due to the biased shape of the tabs 16, the suture can be readily threaded through the opening 20 from the bottom of the device 12. The opening 20 can have a diameter, or narrowest width, that is slightly smaller than the diameter of the suture such that the tabs 16 are forced to deflect upward and outward a small amount when the suture is inserted from the bottom of the device. In a static state with a suture positioned in the opening 20, the tabs 16 can be slightly elastically deformed and thereby biased against the suture to prevent the suture from sliding. As used herein, the terms "elastic," "elastically," and "elasticity" are used in a broad sense to indicate any resilient deformation that tends to naturally return to its pre-deformed state, and these terms include the related concepts of superelasticity and pseudoelasticity. When tension is applied on an upper end of the suture, the tabs 16 deflect slightly further in the upward and radially outward directions, increasing the size of the opening 20 enough to allow the suture to slide through the opening 20 in the upward direction. However, when tension is applied on the lower end of the suture, the suture pulls the tabs 16 downward causing the tabs to pinch closer together, increasing their grip on the suture, and preventing the suture from sliding downward. Biased devices, such as the device 12, can be positioned with the bottom surface of the outer body 14 against a bearing surface (e.g., a surface of prosthetic device or a surface of native tissue) to prevent the suture and the device from moving in the direction of that bearing surface.

Figure 4:
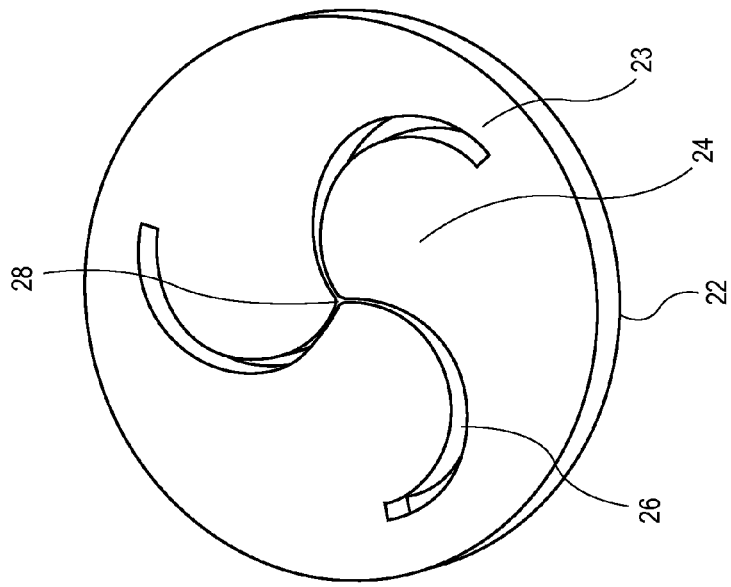
FIG. 4 is a perspective view of another exemplary suture clip.

FIG. 4 shows an exemplary embodiment of an enclosed, non-biased suture securement device 22. The device 22 comprises an annular outer body 23 and three inwardly extending tabs 24 separated by three curved slits 26 that join at a common center opening 28. The device 22 is termed "non-biased" because the tabs 24 do not project out of plane in either axial direction when a suture is not positioned in the opening 28. Thus, non-biased devices are not inherently biased in one direction or the other, though they may become biased in one direction once a suture in inserted. Like in the device 12, the opening 28 can have a diameter, or narrowest width, that is slightly smaller than the diameter of a suture. As the device 22 is non-biased in its natural state, the suture can be threaded through the opening 28 from either the top or the bottom equivalently. Because the opening 28 in its natural state is narrower than the suture, when the suture is inserted the tabs 24 are forced to deflect out of plane a small amount in the direction the suture is inserted to increase the size of the opening 28 enough to allow the suture to pass through. When a suture is inserted into the opening 28 from one side, the tabs 24 bend toward the other side, creating an out-of-plane aspect to the tabs 24 and making the device biased. For example, when a suture is inserted from the bottom side of the opening 28, the tabs 24 bend upwardly to increase the size of the opening 28 enough to receive the suture. At that point, the tabs 24 are biased to allow the suture to slide upwardly with limited resistance but prevent the suture from sliding downwardly. The curved shaped of the slits 26 can provide a more desirable stress-strain distribution across the tabs 24 for certain materials, such as Nitinol, compared to the linear, radial slits 18 in the device 12, which can be more desirable for other materials, such as stainless steel.

Figure 5B:
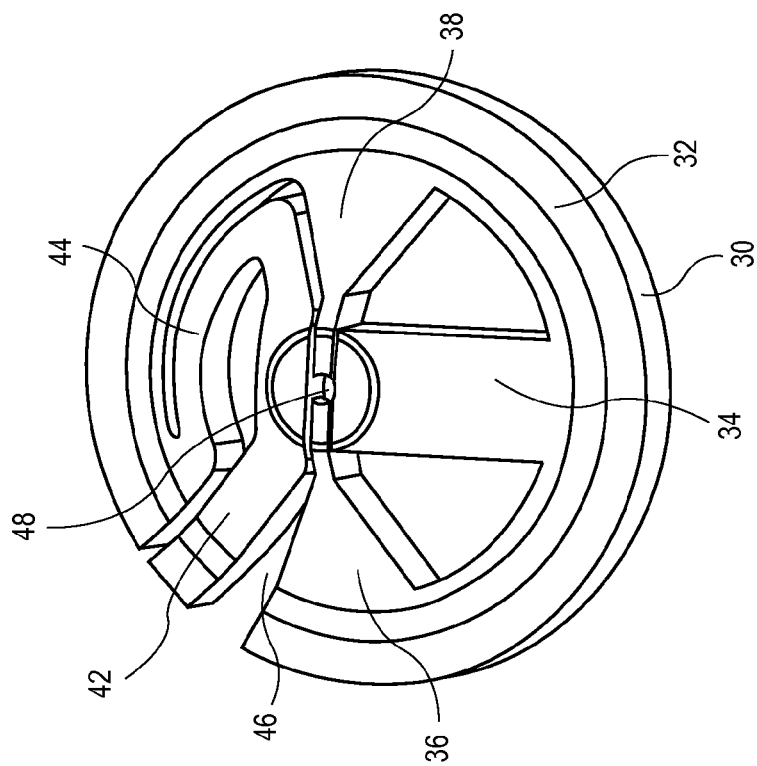
FIG. 5B is a perspective view of the suture clip of FIG. 5A.
Figure 5A:
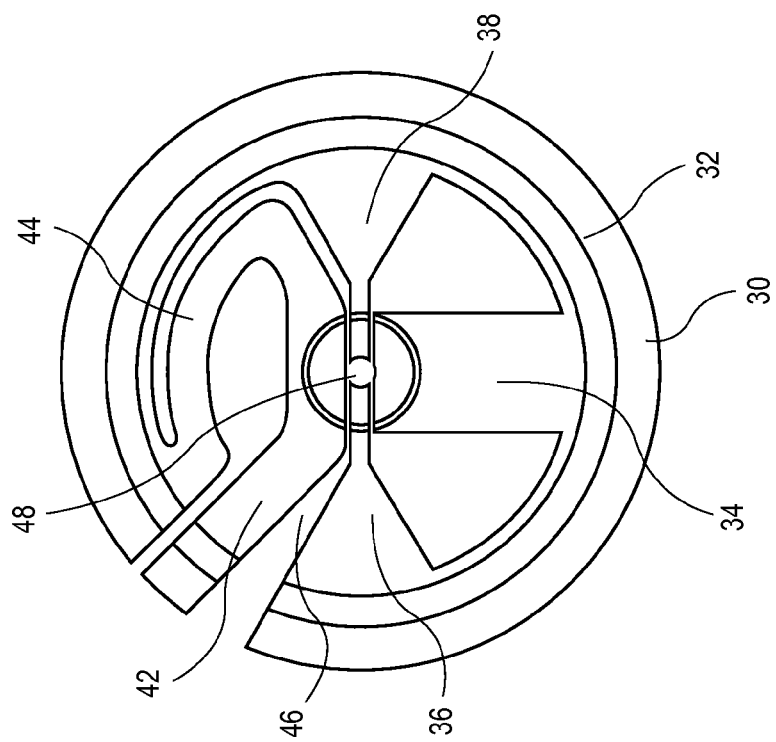
FIG. 5A is a plan view of another exemplary suture clip.

FIGS. 5A and 5B show an exemplary embodiment of an open, biased suture securement device 30. The device 30 comprises an outer body 32 and a first tab 34, second tab 36, third tab 38 and a spring arm 42, each of which extends inwardly and out-of-plane from the outer body 32 toward a central opening 48. The device 30 is "open" because the central opening 48 communicates with a radial slit 46 that allows an intermediate portion of a suture to be laterally slid into the opening 48 instead of an end of the suture being threaded through the opening from the top or the bottom. The spring arm 42 comprises a spring element 44 that allows the arm 42 to elastically deform radially outwardly toward the outer body 30. When a suture is slid through the slit 46 toward the opening 48, the spring arm 42 can elastically deform to widen the slit 46 and allow the suture to enter the opening 48. In some embodiments, a tool can be used to deform the spring arm 42 during deployment, though the tapered walls of the slit 46 can allow the spring arm 42 to be sufficiently deformed with relatively little radially-inward force on the suture. A greater force on the suture is required to deform the spring arm 42 once the suture is in the opening, due to the shorter lever arm and the lack of the tapered walls for mechanical advantage. In its natural state, the opening 48 is slightly smaller than the diameter of the suture such that radial pressure is applied on the suture in the opening 48 even when there is no tension on the suture. Due to the out-of-plane dimensions of the tabs 34, 36, 38 and spring arm 42, the suture is allowed to slide upwardly through the opening 48 with little resistance, but is prevented from sliding downwardly through the opening as the tabs collapse and pinch the suture.

Figure 6B:
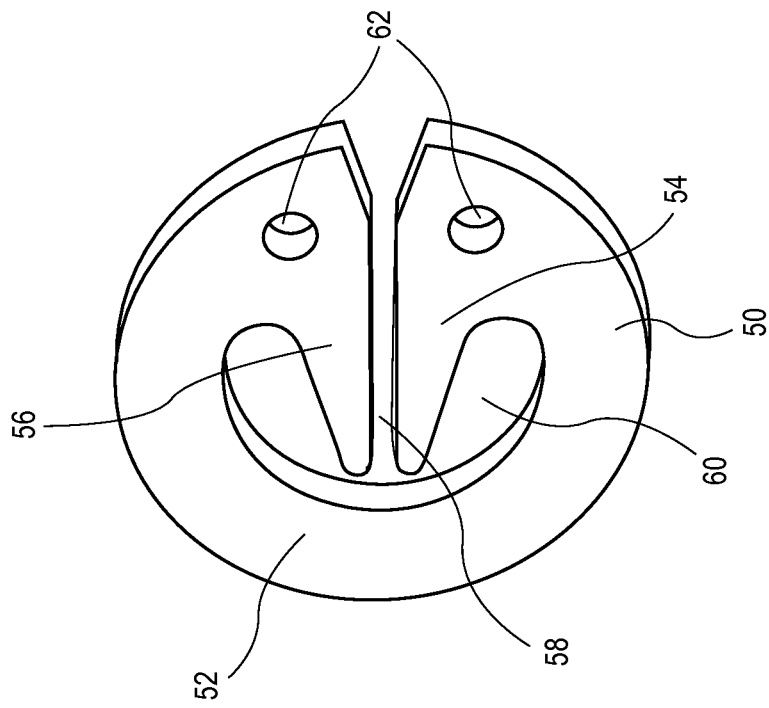
FIG. 6B is a perspective view of the suture clip of FIG. 6A.
Figure 6A:
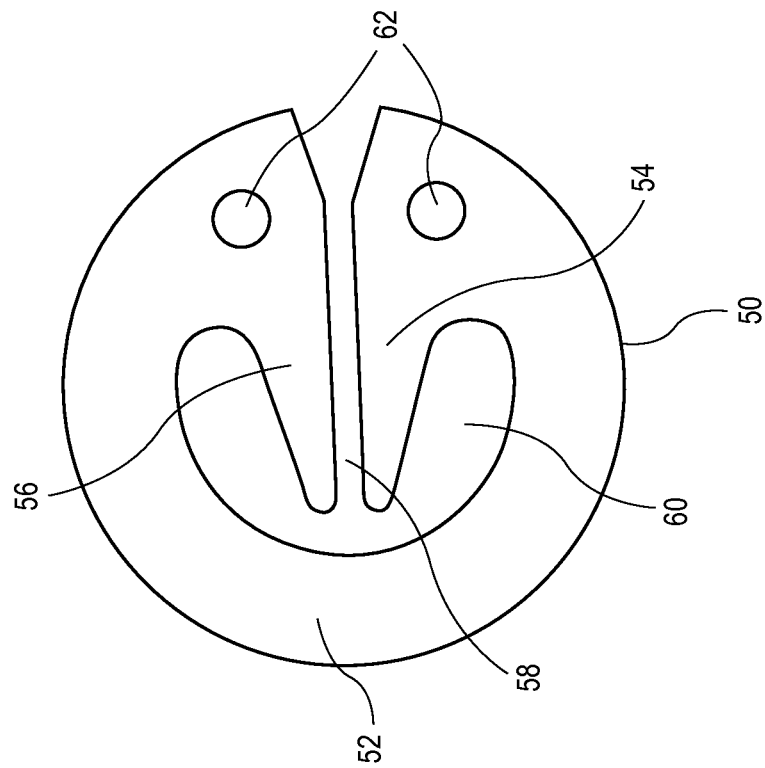
FIG. 6A is a plan view of another exemplary suture clip.

FIGS. 6-8 show exemplary embodiments of open, non-biased suture securement devices. FIGS. 6A and 6B show a device 50 that comprises an outer body 32, a first arm 54, and a second arm 56. The first and second arm a separated by a slit 58 that extends inwardly from the outer perimeter of the device to an open region 60. The width of the slit 58 between the arms 56 and 54 can be slightly smaller than the diameter of a suture. The slit 58 can be tapered near the outer perimeter to facilitate inserting a suture into the narrow portion of the slit between the arms. The open region 60 can make the outer body more flexible to allow the arms 54, 56 to be separated to receive a suture. The device 50 can also comprise openings 62 on either side of the slit 58 to facilitate using a tool (e.g., a tool similar to needle-nose pliers) to forcibly separate the arms 54, 56. When two or more sutures are secured with the device 50, the sutures are desirably oriented side-by-side along the length of the slit 58, rather than being stacked in the width direction of the slit. In some embodiments, the device 50 does not deform out-of-plane when the suture is inserted, but rather only deforms in-plane and applies an in-plane pinching force on the suture that prevents the suture from sliding in either axial direction. In other embodiments, both arms 54, 56 can deform out of plane in the same direction, creating a biased device that prevents the suture from sliding in only on axial direction. In still other embodiments, the arms 54, 56 can deform out-of-plane in opposite directions, with the outer body 52 twisting, such that the suture is prevented from sliding in both directions.

FIGS. 7A and 7B show another open, non-biased device 64 that is similar to the device 50. The device 64 comprises an outer body 66, a first arm 68, and a second arm 70. The first and second arm a separated by a slit 72, which extends inwardly from the outer perimeter of the device to another slit portion 74 that extends at right angles from the slit 72 to an open region 76. The width of the slit 72 between the arms 68, 70 can be slightly smaller than the diameter of a suture. The slit 72 can be tapered near the outer perimeter to facilitate inserting a suture into the narrow portion of the slit between the arms. The open region 76 can make the outer body more flexible to allow the arms 68, 70 to be separated to receive a suture. In use, one or more sutures are held within the slit 72 by the pinching force of the arms 68, 70. Because the slits 72 and 74 are at right angles, the sutures are less likely to slide out of the slit and into the open region 76, as compared to the device 50. Also, the width of the slit 74 can be made smaller that the slit 72, and in some cases the slit 74 is closed with the arms 74 and 70 touching each other.

The device 64 can also comprise openings 78 on either side of the slit 72 to facilitate using a tool to forcibly separate the arms. In some embodiments, the device 64 does not deform out-of-plane when the suture is inserted, but rather only deforms in-plane and applies an in-plane pinching force on the suture that prevents the suture from sliding in either axial direction. In other embodiments, both arms 68, 70 can deform out of plane in the same direction, creating a biased device that prevents the suture from sliding in only on axial direction. In still other embodiments, the arms 68, 70 can deform out-of-plane in opposite directions, with the outer body 66 twisting, such that the suture is prevented from sliding in both directions. FIG. 8 shows a device 80 that is similar to the device 64, except that it further comprises a notch 82 in each arm 84, 86 adjacent to the slit 72. The notches 82 help hold the two sutures in the slit 72 in a desirable position, and help prevent the sutures from sliding out of the slit.

Figure 9B:
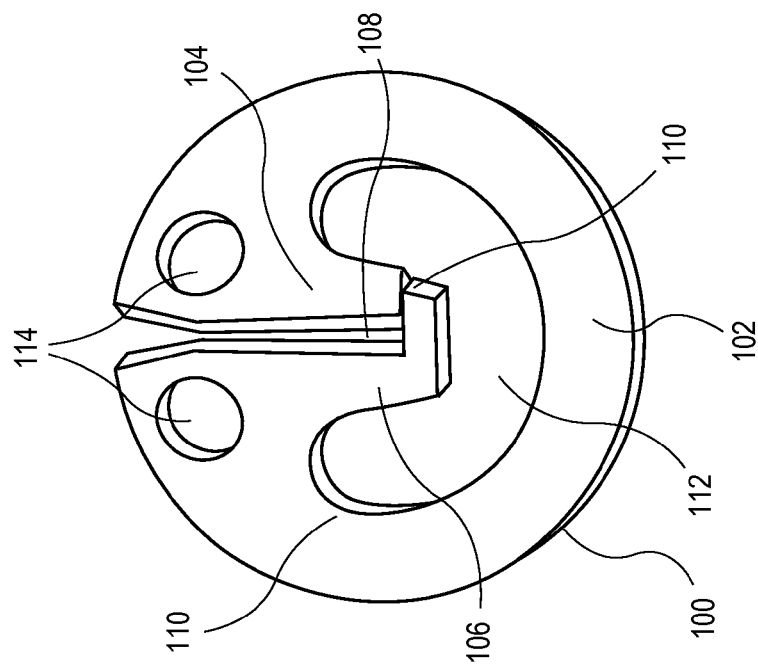
FIG. 9B is another perspective view of the suture clip of FIG. 9A.
Figure 9A:
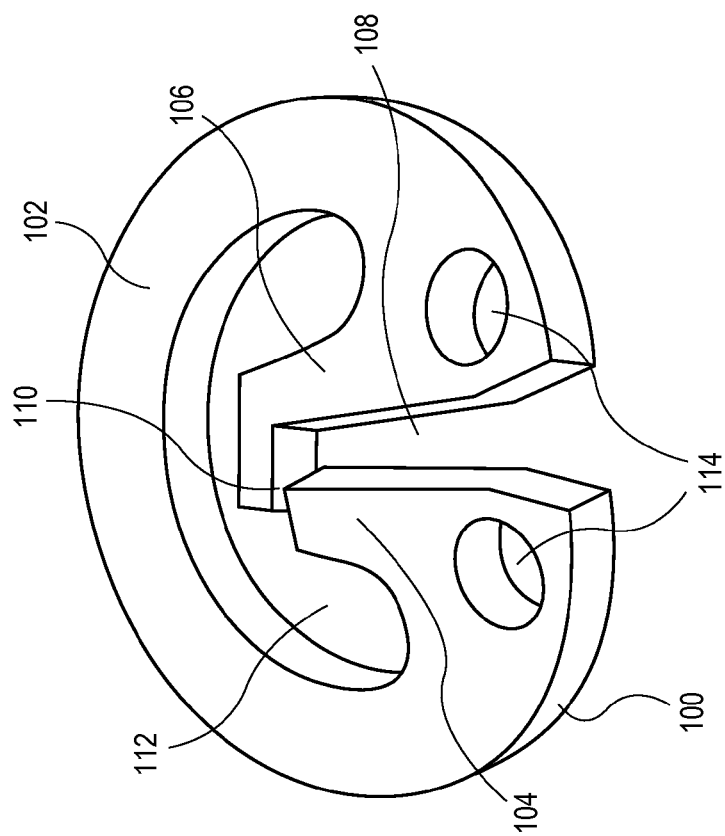
FIG. 9A is a perspective view of another exemplary suture clip.

FIGS. 9A and 9B show an open, biased device 100 that is similar to the device 64, except that it includes an out-of-plane dimension. The device 100 comprises an outer body 102, a first arm 104, and a second arm 106. The first and second arm a separated by a slit 108 that extends inwardly from the outer perimeter of the device to another slit portion 110, which extends at right angles from the slit 108 to an open region 112. The width of the slit 108 between the arms 104, 106 can be slightly smaller than the diameter of a suture. The slit 108 can be tapered near the outer perimeter to facilitate inserting a suture into the narrow portion of the slit between the arms. The open region 112 can make the outer body more flexible to allow the arms 104, 106 to be separated to receive a suture. The device 100 can also comprise openings 114 on either side of the slit 108 to facilitate using a tool to forcibly separate the arms. The arms 104 and 106 can extend upwardly, out-of-plane from the outer body 102 to create a bias that allows the suture to slide upwardly with little resistance but prevents the suture from sliding downwardly.

Figure 10B:
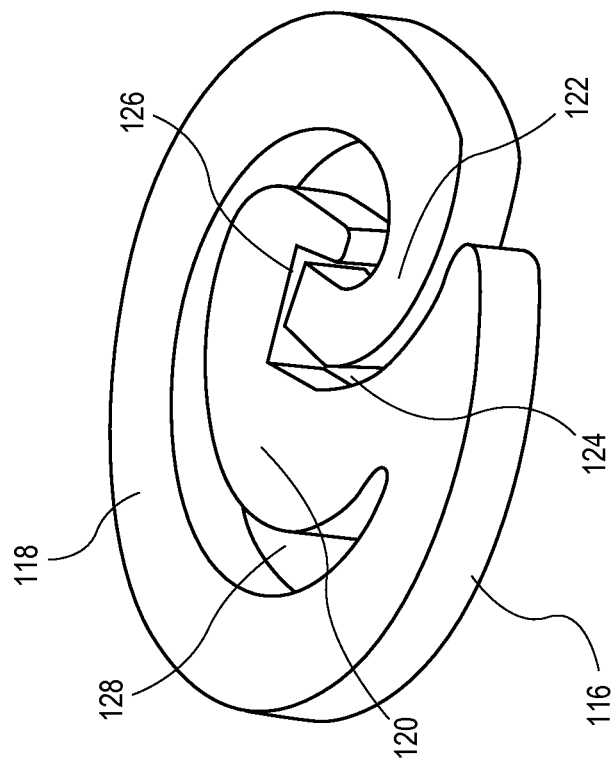
FIG. 10B is a perspective view of the suture clip of FIG. 10A.
Figure 10A:
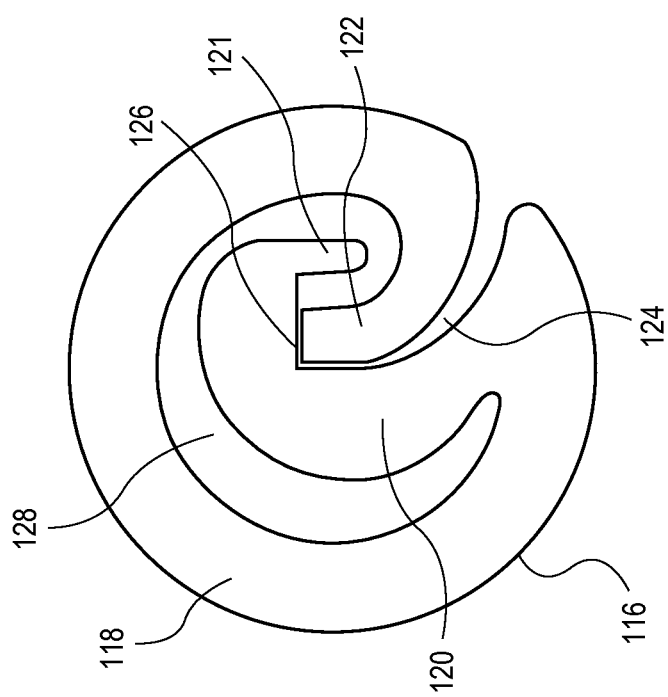
FIG. 10A is a plan view of another exemplary suture clip.
Figure 12B:
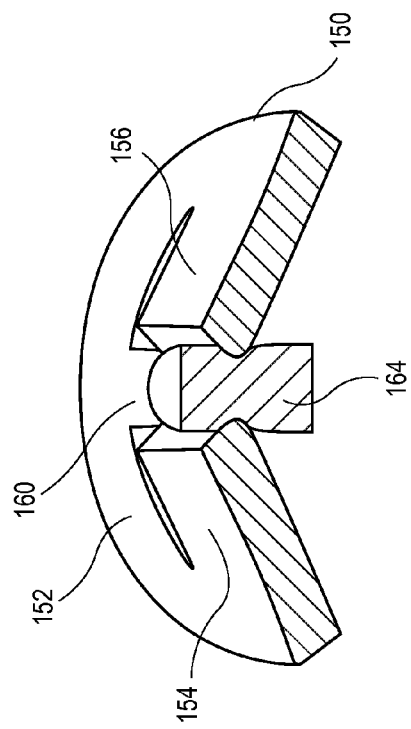
FIG. 12B is a sectional perspective view of the suture clip of FIG. 12A engaged with a suture.
Figure 12D:
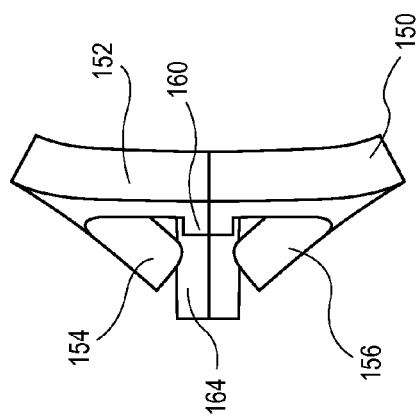
FIG. 12D is a side view of the suture clip of FIG. 12A.
Figure 12A:
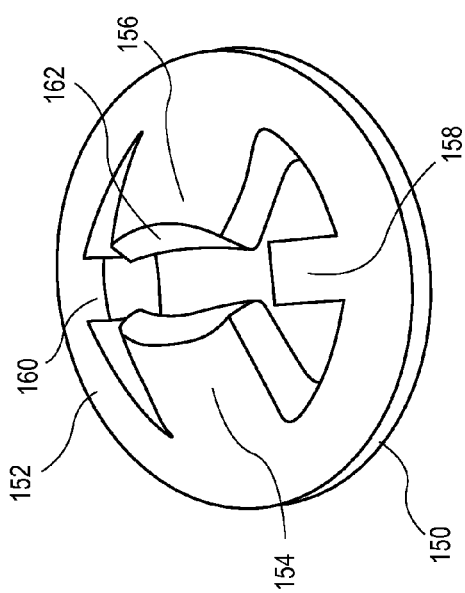
FIG. 12A is a perspective view of another exemplary suture clip.
Figure 12C:
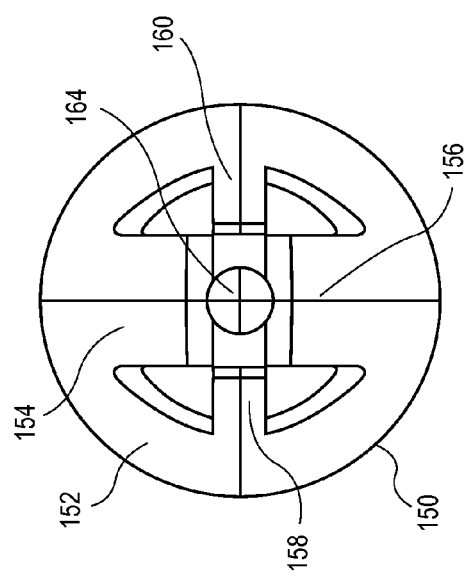
FIG. 12C is a plan view of the suture clip of FIG. 12A.

FIGS. 10A and 10B show another open, non-biased device 116. The device 116 comprises an outer body 118, a first arm 120 and a second arm 122. The first and second arms are separated by a curved slit 124 that extends inwardly from the outer perimeter of the device to another slit portion 126, which extends at right angles from the slit 124 to an open region 128. The narrowest width of the slit 124 can be slightly smaller than the diameter of a suture to retain the suture within the slit 124. The slit 124 can be tapered from the outer perimeter to facilitate inserting a suture into the narrowest portion of the slit 124. The open region 128 can circumscribe an arc of about 270° through the device 116, making the outer body 118 more flexible to allow the arms 120, 122 to be separated to receive a suture. The arm 120 can be partially curled around the end of the arm 122 and can comprise an end portion 121 that blocks the arm 122 from being separated too far from the first arm 120, thereby limiting the width of the slit 124.

FIGS. 11A and 11B show embodiments of a closed, non-biased suture fastening device 130. The device 130 comprises a generally disk-shaped body having an annular outer edge 132 and two tabs 134, 136 that extend inwardly from the outer edge 132. Each tab 134, 136 is shaped generally in a half-circle. The tabs 134, 136 are separated from the outer body at their sides by curved slots 138, 140 and are separated from each other by a straight slit 142 generally bifurcating the device 130. The curved slots 138, 140 and middle slit 142 connect to each other but do not intersect with an outer edge 132, thus forming a "closed"

generally H-shaped opening extending from one face of the device to the other. One or more sutures 143 can be inserted into the slit 142 from either the top or the bottom, deflecting both tabs 134, 136 in the direction of insertion, as shown in FIG. 11B. Once the sutures 143 are inserted as shown in FIG. 11B, the device 130 becomes biased and allows the sutures to move axially upward with little resistance but prevents the sutures from moving axially downward. In some embodiments, the gripping edges of the tabs 134, 136 can be sharp (see FIG. 11A), which can provide better grip on the sutures, and in other embodiments the gripping edges of the tabs can be rounded (see FIG. 11B), which can reduce the likelihood of damaging and/or cutting the sutures. In some implementations of the device 130 (not shown), the two tabs 134, 136 can be elastically deformed in opposite directions with one tab bending upwardly out-of-plane and the other tab bending downwardly out-of-plane. This can lock the sutures from sliding in either direction through the device 130. The two sutures 143 shown in FIG. 11B can correspond to free ends of the sutures 6 shown in FIG. 2, for example.

FIG. 11C shows a device 144 that is a variation of the device 130 wherein the gripping surfaces of the tabs 134, 136 comprise notched or recess regions 145 that can help contain the sutures within the slit 142 and prevent them from sliding into the curved slits 138, 140.

FIG. 11D shows a still further variation of the suture fastening device 146 having a flat generally disk-shaped body having an annular outer edge 132' and two tabs 134', 136' that extend inwardly therefrom. As in FIG. 11A, each tab 134', 136' is shaped generally in a half-circle. The tabs 134', 136' are separated from the outer body at their sides by curved slots 138', 140' and are separated from each other by a slit 142' that has a straight midsection. Once again, the curved slots 138', 140' and middle slit 142' connect to each other but do not intersect with an outer edge of the body 132', thus forming a "closed" generally H-shaped opening extending from one face of the device to the other. One or more sutures can be inserted into the slit 142 from either the top or the bottom, deflecting both tabs 134, 136 in the direction of insertion, as was shown in FIG. 11B. Once the sutures 143 are inserted in the slit 142, the device 146 becomes biased and allows the sutures to move axially upward with little resistance but prevents the sutures from moving axially downward. As mentioned above, the gripping edges of the tabs 134, 136 may be sharp for better grip on the sutures, or rounded to reduce the likelihood of damaging and/or cutting the sutures.

To help retain sutures in the midsection of the slit 142', the slit includes serpentine sections 147 on either side. The tabs 134', 136' are identical, or mirror images of each other, though one may be larger than the other. Small circular enlargements 148 on the terminal end of each curved slot 138', 140' facilitate bending of the tabs 134', 136' and act as stress relievers to reduce the chance of fracture at those points. Two semi-circular cutouts 149 are provided on opposite sides of the outer edge 132' perpendicular to the straight section of the slit 142'. The cutouts 148 provide orientation features for the suture fastening device 146 that cooperate with features on a tool (not shown) which can hold and deploy multiple devices in series.

FIGS. 12A-12D show an embodiment of a closed, biased device 150. The device 150 comprises an annular outer body 152, and two engagement tabs 154, 156 and two side tabs 158, 160 extending inwardly from the outer body 152. The tabs 154, 156 and/or the tabs 158, 160 can also extend upwardly out-of-plane from the outer body 152. The engagement tabs 154, 156 can comprise concave engagement surfaces 162 to keep the suture 164 centered between them. The side tabs 158, 160 can prevent the suture 164 from sliding laterally out from between the engagement arms 154, 156. The engagement arms 154, 156 are biased to allow the suture 164 to slide upwardly through the device 150 with little resistance but prevent the suture from sliding downwardly through the device.

Figure 13:
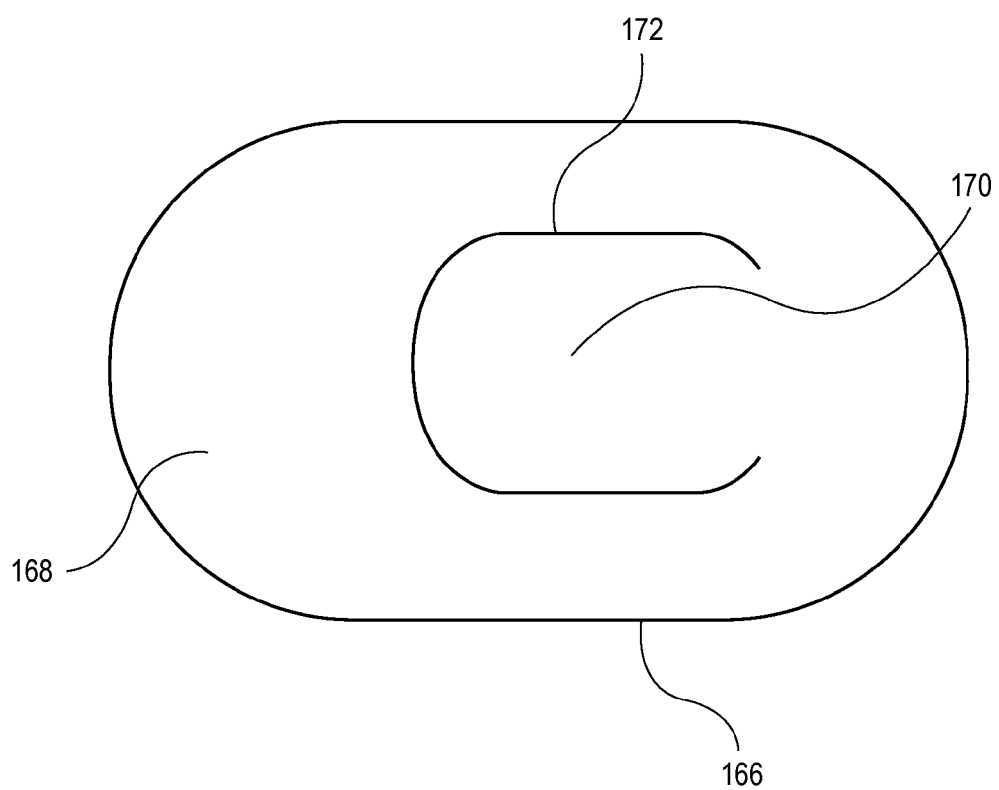
FIG. 13 is a plan view of another exemplary suture clip.

FIG. 13 shows an embodiment of a closed, non-biased device 166 comprising a generally oblong or oval shaped outer body 168 and a single tab 170. The tab 170 is separated from the outer body on three sides via a cut 172 that forms a general "C" shape. For example, the cut 172 can be laser cut into a single sheet of material to form the tab 170. The tab 170 can be elastically bent either direction out-of-plane from the outer body 168 to allow a suture to be inserted through the cut 172. After a suture in introduced through the cut 172, the device 166 becomes biased to allow the suture to slide in the direction the tab 170 is bent with little resistance but prevent the suture from sliding in the opposite direction.

The devices of FIGS. 3-13 can vary in thickness, though the thickness is generally smaller than the dimensions perpendicular to the thickness. Increased thickness generally results in a more rigid device that provides more resistance to the suture sliding through the device. The devices of FIGS. 3-13 can also vary in the dimensions perpendicular to the thickness dimension. In some embodiments, the device can have an outer diameter of about 2 mm to about 5 mm, or larger.

The disclosed suture securement devices can comprise any resiliently deformable, corrosion-resistant, biocompatible material, such as stainless steel, cobalt-chrome (Co—Cr), Elgiloy, MP35N, and Nitinol. Some embodiments can comprise more than one material, such as a more rigid material for the outer body and a more elastically flexible material for the arms/tabs. Desirably, the disclosed embodiments are comprised of material with a recoverable strain that is sufficient to retain sutures, such as a recoverable strain that ranges from about 5% to about 15%.

Figure 14:
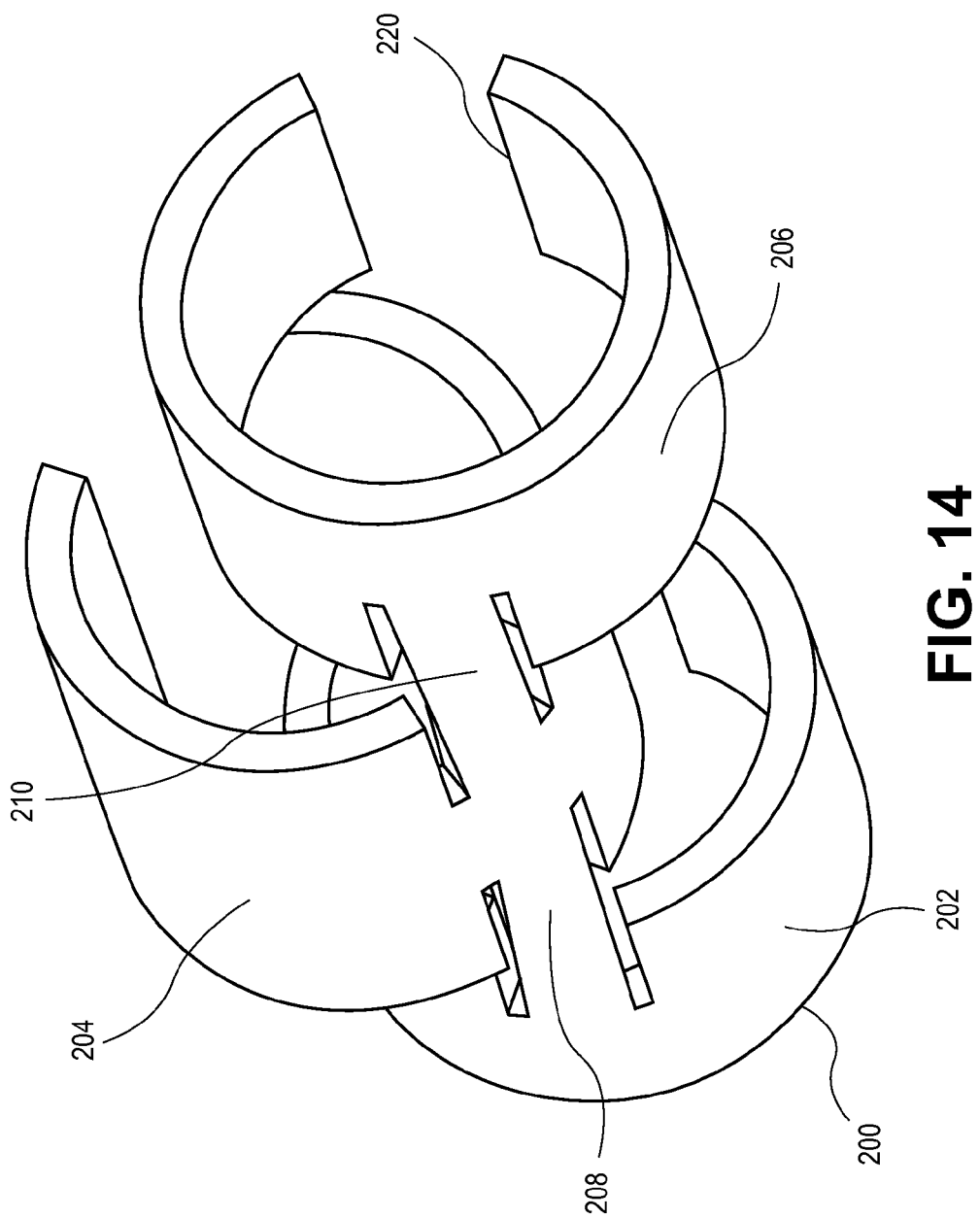
FIG. 14 is a perspective view of an exemplary suture securement device.
Figure 15:
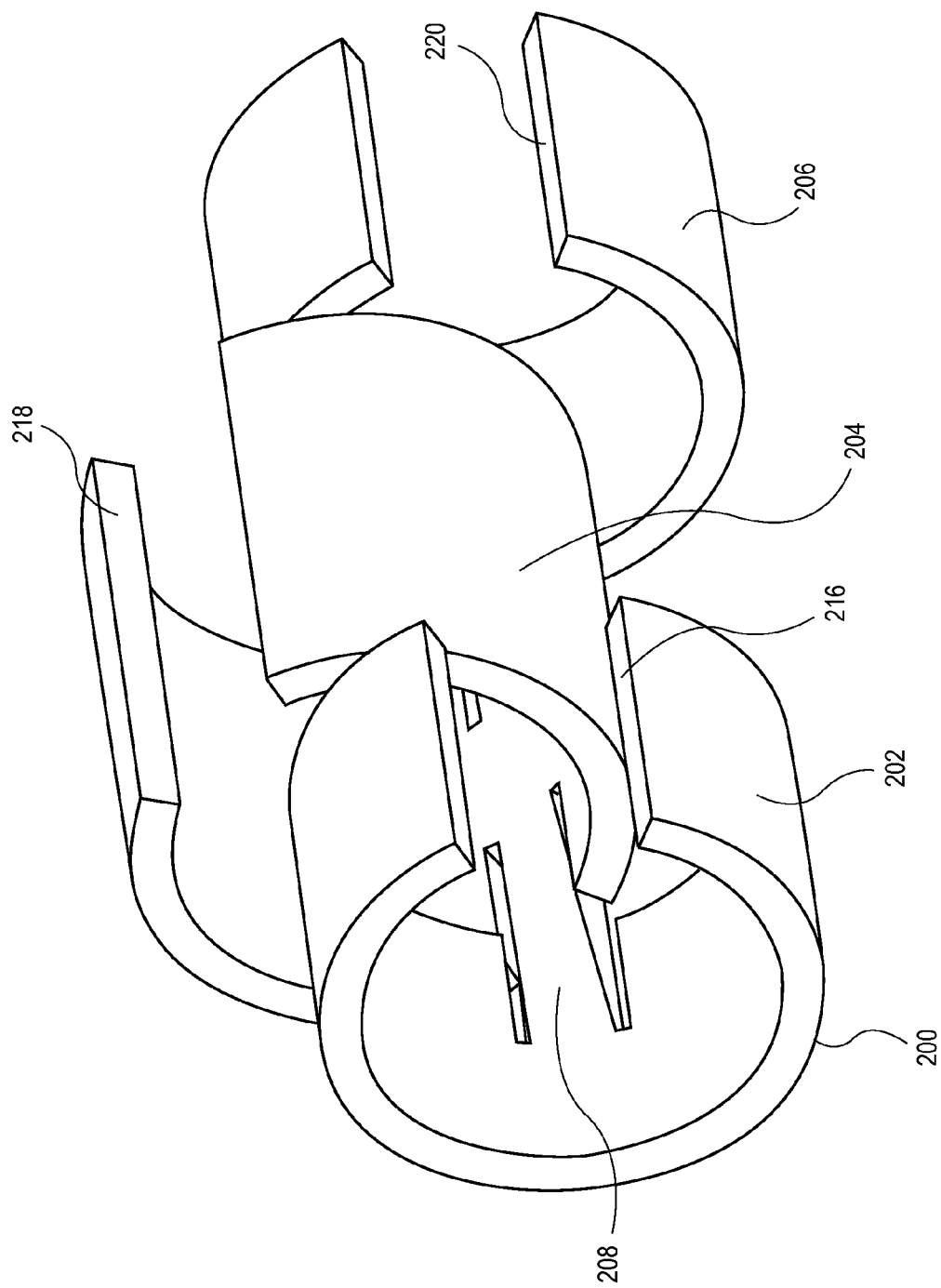
FIG. 15 is another perspective view of the suture securement device of FIG. 14.
Figure 16:
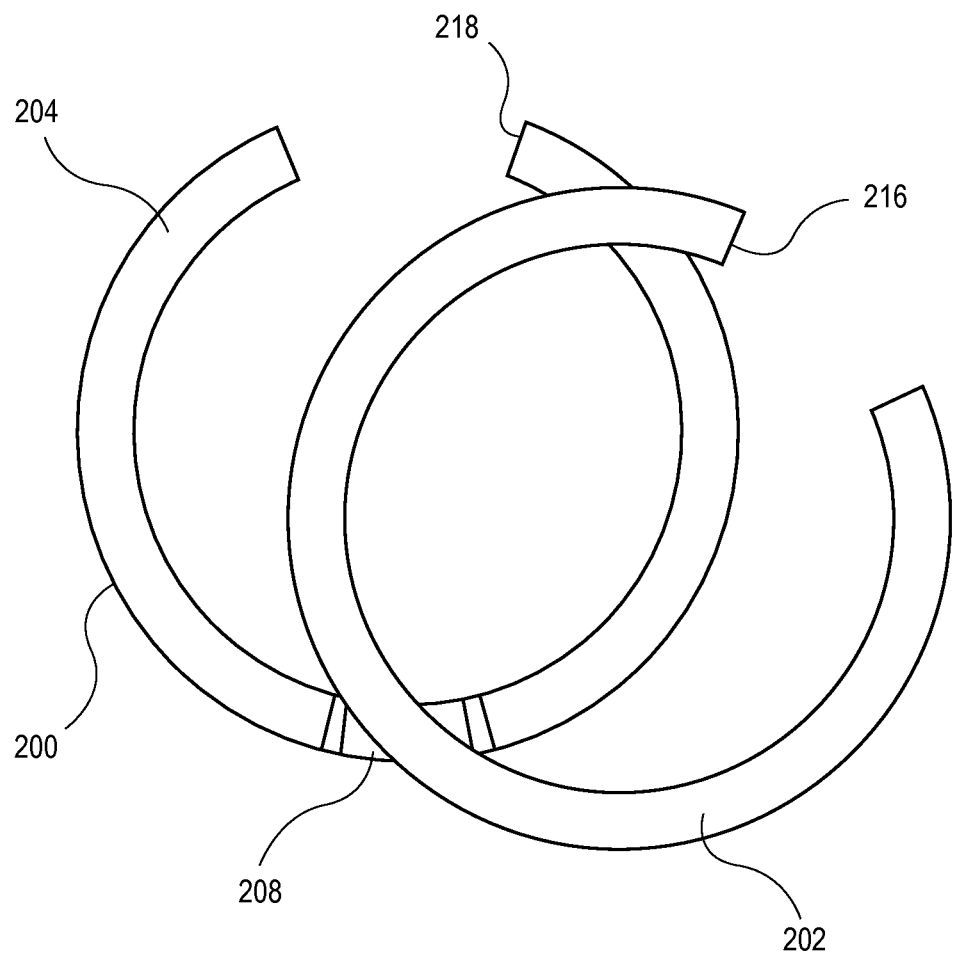
FIG. 16 is an end view of the suture securement device of FIG. 14.

FIGS. 14-17 show an exemplary suture securement device 200. The device 200 comprises three or more sections that are coupled together along an elastic spine. The device 200 can comprise a first section 202, second section 204, and third section 206, with the first and second sections coupled by a first spine segment 208 and the second and third sections coupled together by a second spine segment 210. In other embodiments, the device can comprise four or more similar sections coupled by three or more spine segments. As shown in FIG. 15, each section can comprise an annular wall (e.g., cylindrical or otherwise) that is open at one side opposite the spine. The section 202 comprises an opening 216, the section 204 comprises an opening 218, and the section 206 comprises an opening 220. In its natural state, as shown in FIGS. 14-16, the device 200 is configured with at least one section being misaligned from one or both of the other sections (see FIG. 16). The spine segments 208 and 210 are twisted such that the second section 204 is misaligned with the first and thirst sections 202, 204, which can be generally aligned with each other.

Figure 17:
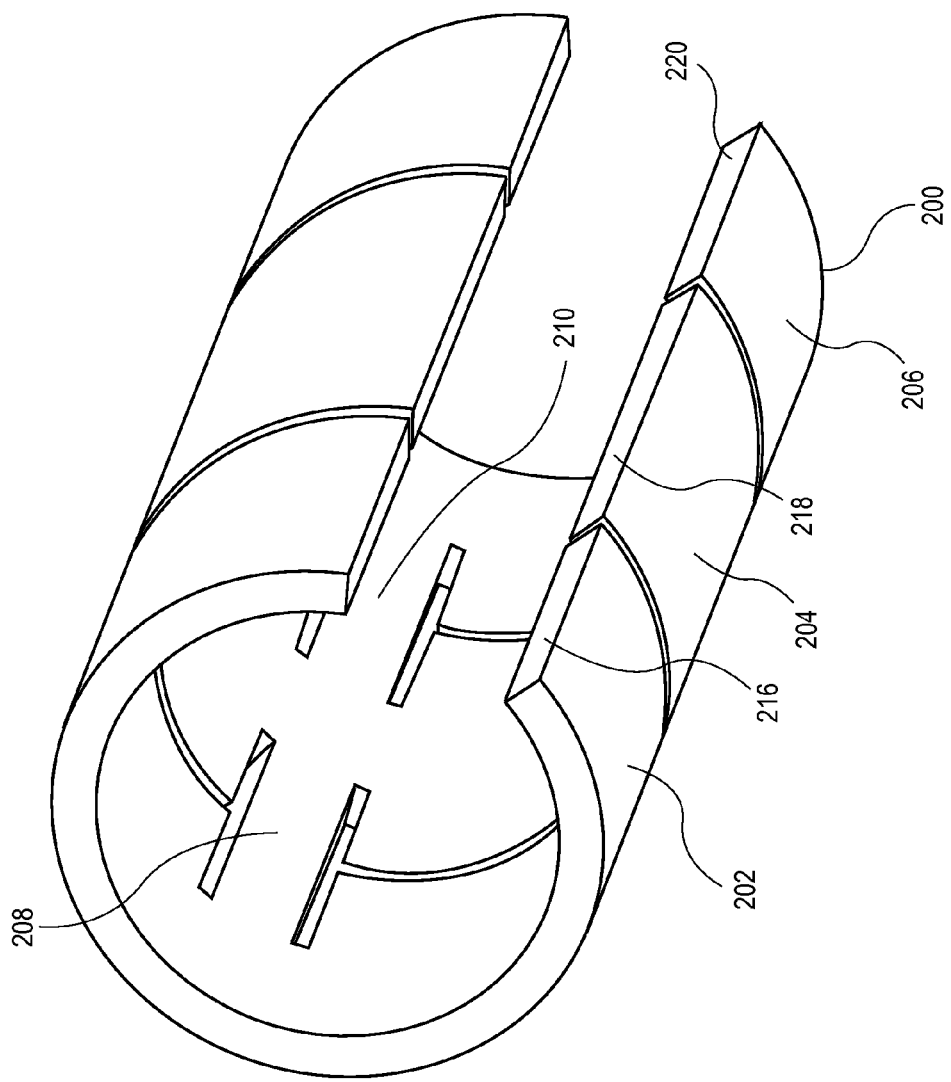
FIG. 17 is a perspective view of the suture securement device of FIG. 14 in a resiliently deformed state.
Figure 18:
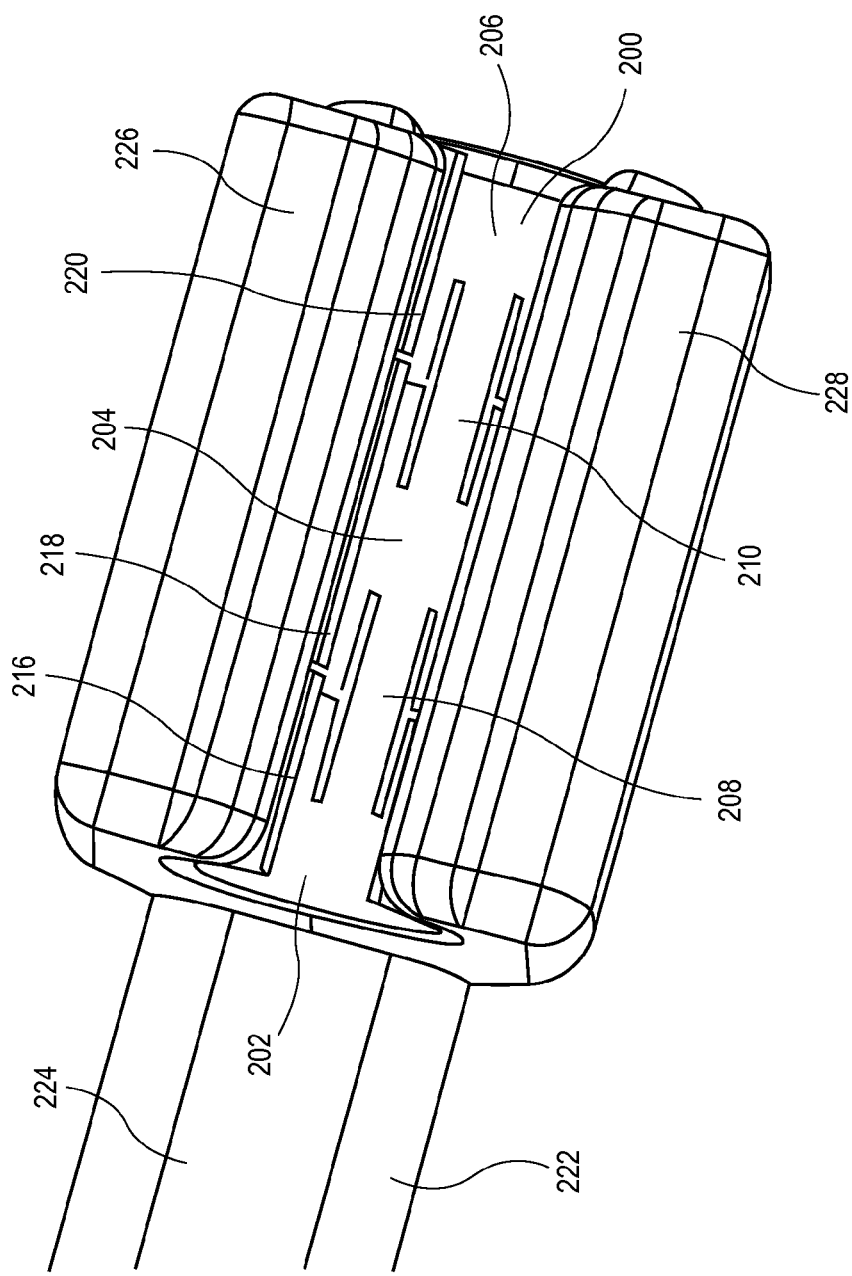
FIG. 18 shows the suture securement device of FIG. 14 being held within an exemplary deployment device.
Figure 19:
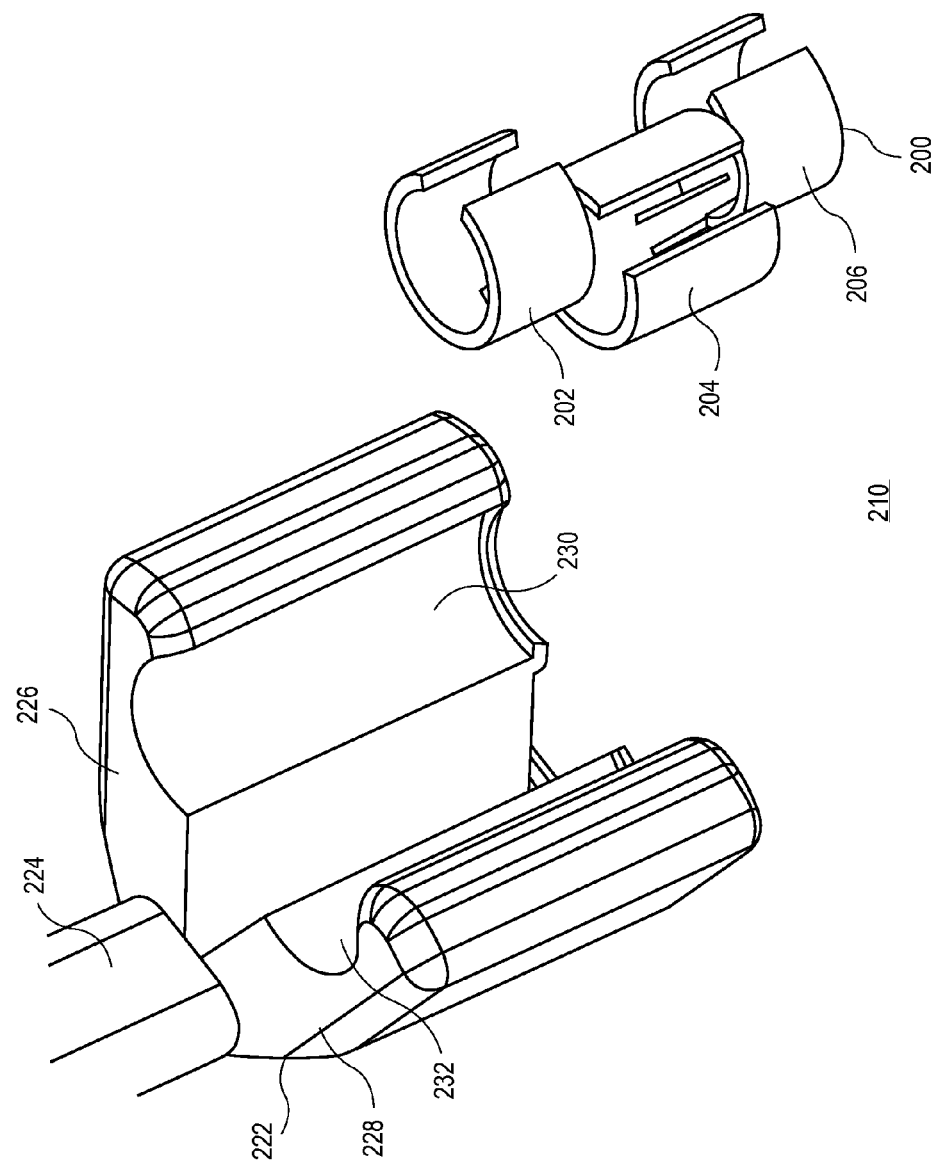
FIG. 19 shows the suture securement device of FIG. 14 released from the deployment device of FIG. 18.
Figure 20:
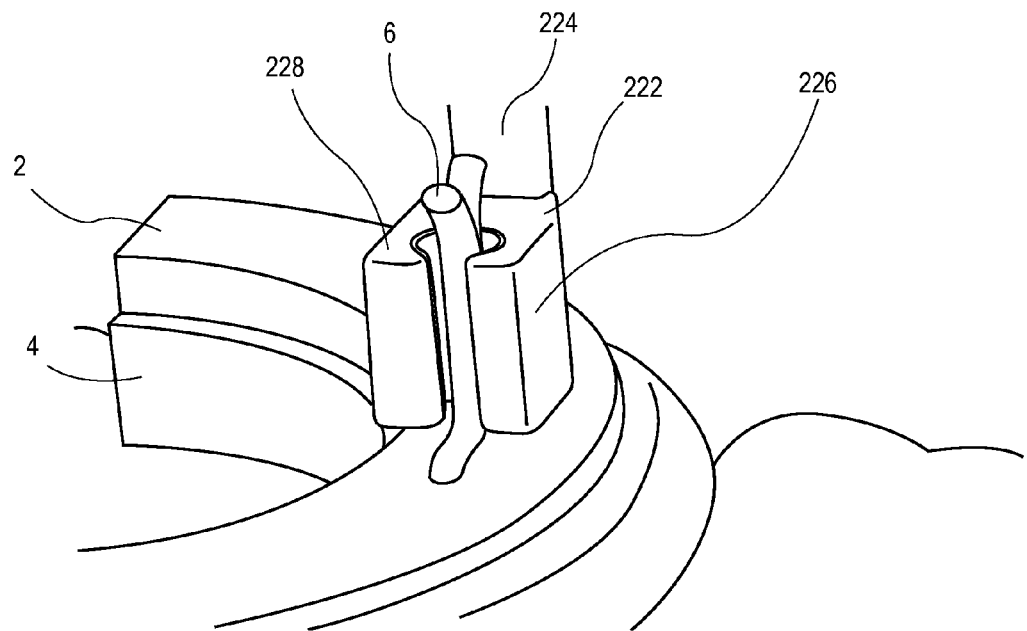
FIG. 20 shows the suture securement device of FIG. 14 positioned around two free suture ends using the deployment device of FIG. 18 to implant a prosthetic device.
Figure 21:
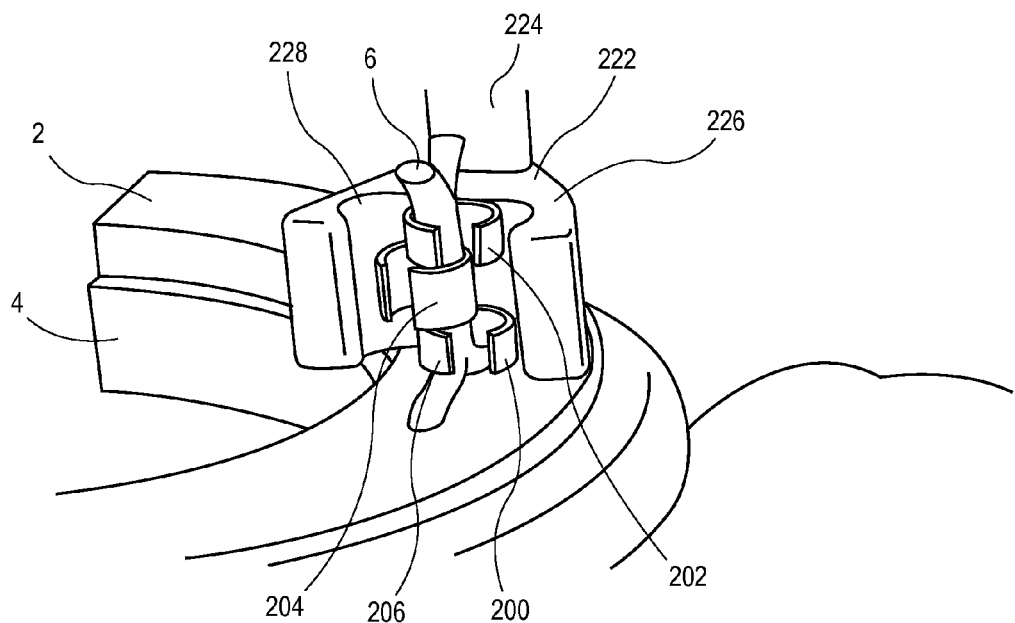
FIG. 21 shows the suture securement device of FIG. 14 freed from the deployment device of FIG. 18 and secured around two suture ends.
Figure 22:
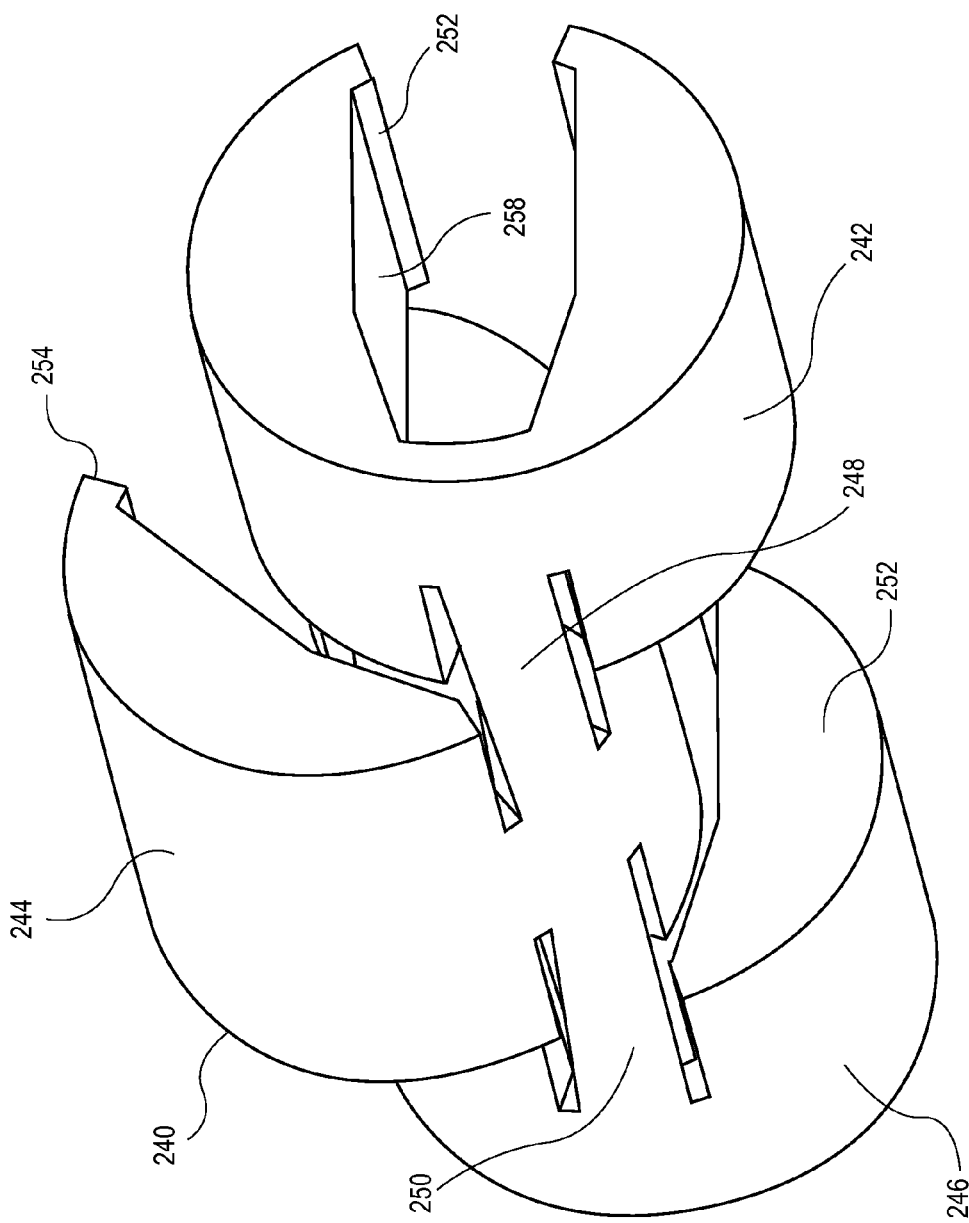
FIG. 22 is a perspective view of another exemplary suture securement device.
Figure 23:
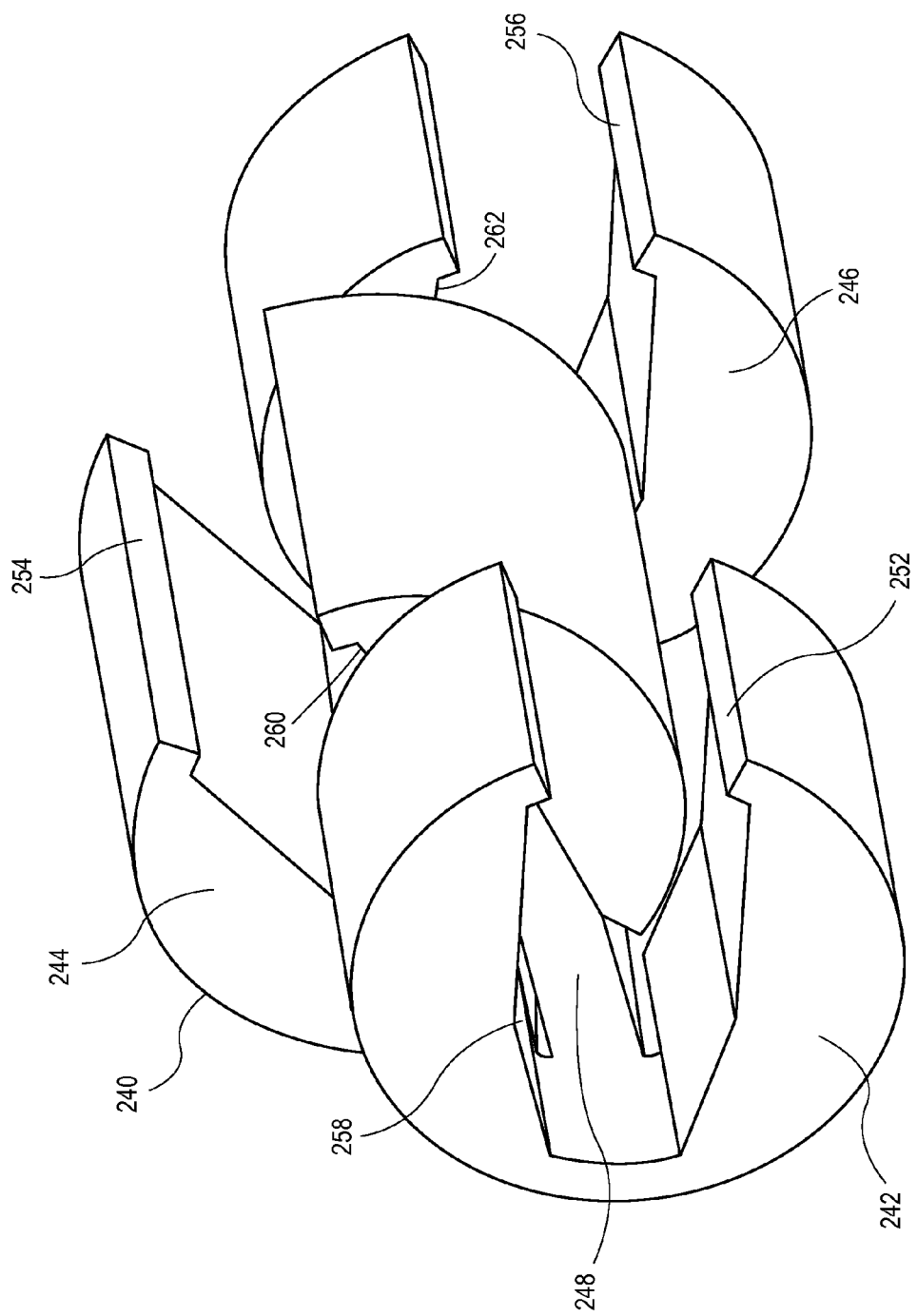
FIG. 23 is another perspective view of the suture securement device of FIG. 22.
Figure 24:
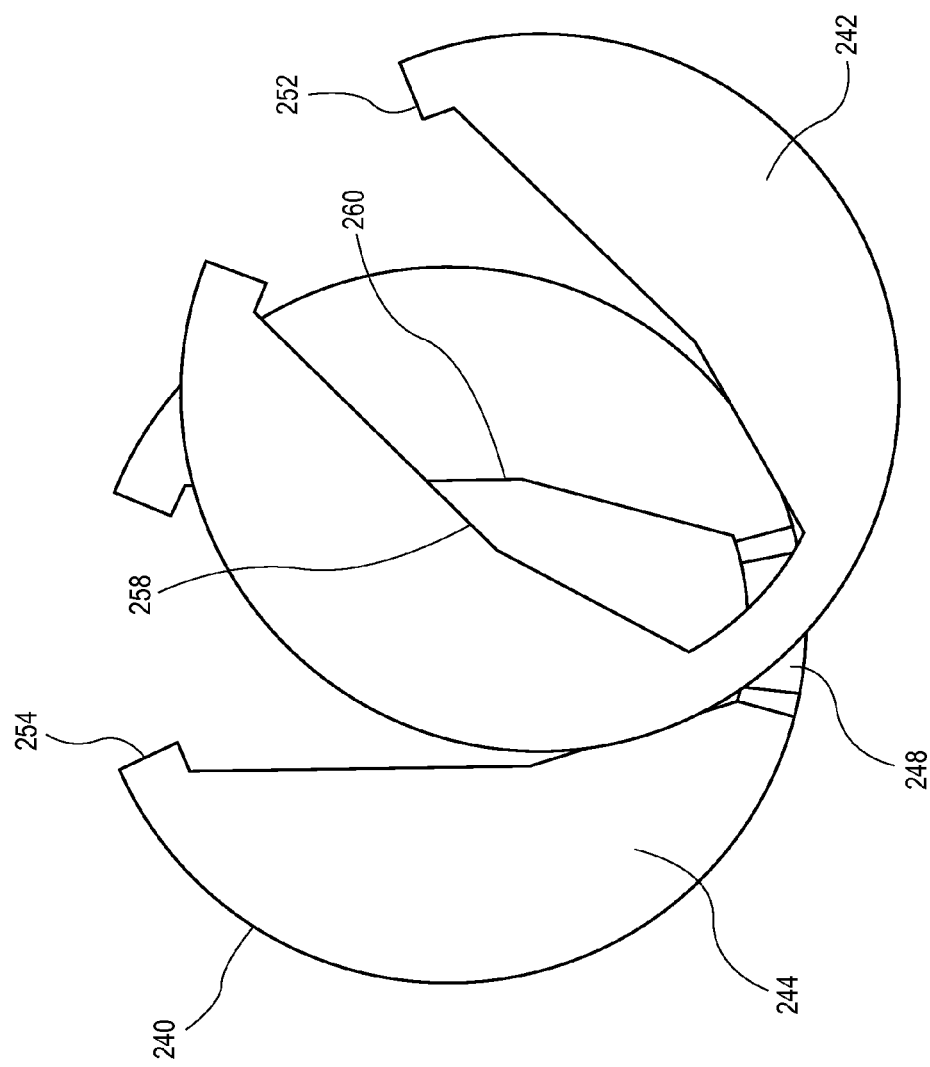
FIG. 24 is an end view of the suture securement device of FIG. 22.
Figure 25:
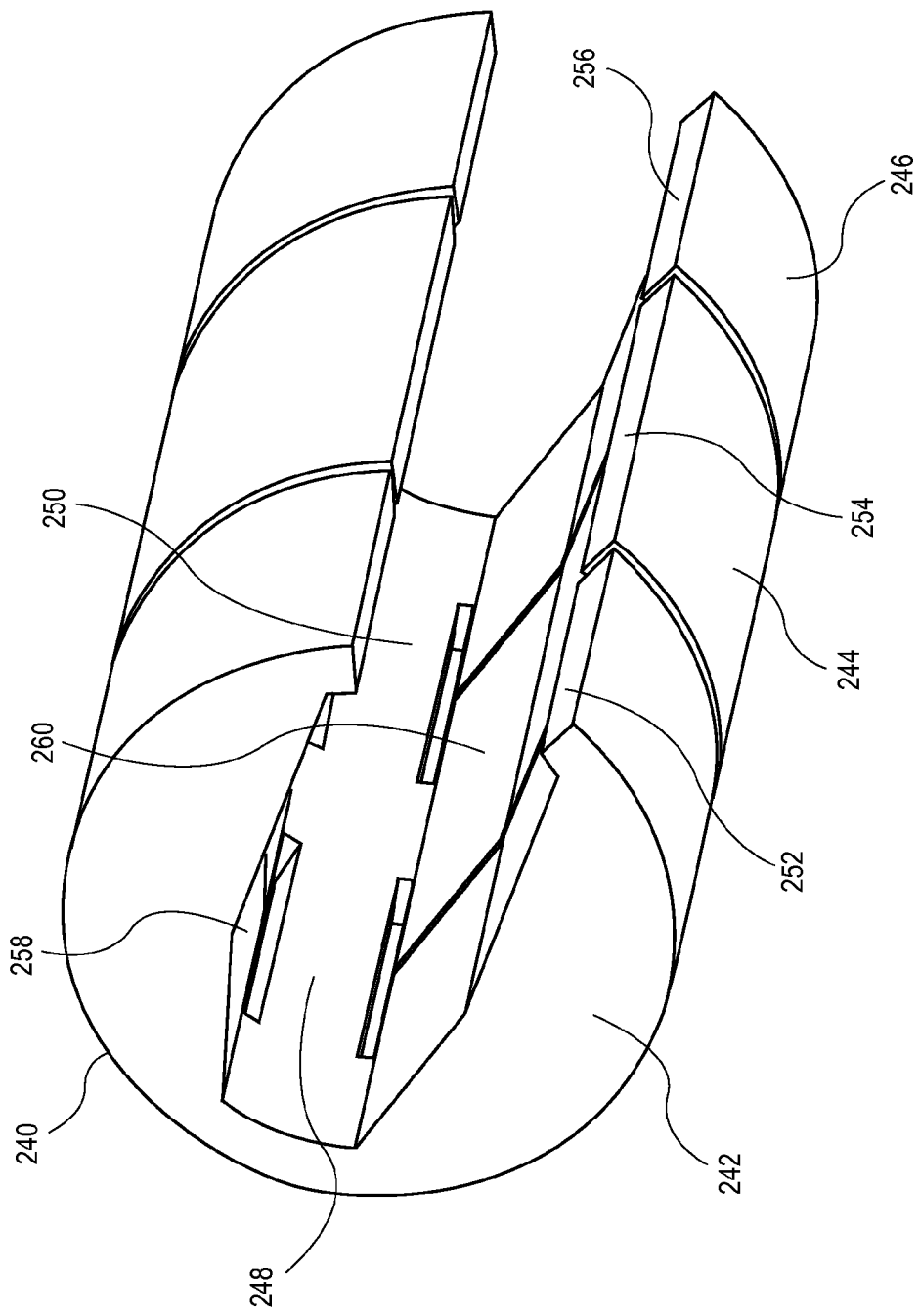
FIG. 25 is a perspective view of the device of FIG. 22 in a deformed configuration.

The device 200 can be elastically deformed to align all of the sections in a cylindrical configuration such that the openings 216, 218, 220 are also aligned, as shown in FIG. 17. As shown in FIGS. 18 and 19, a tool 222 can be used to hold the device 200 in the configuration shown in FIG. 17. The tool 222 can comprise a handle 224, a first jaw 226 and a second jaw 228. The jaws 226, 228 can have rounded inner walls 230, 232, respectively, to hold the device 200 in the configuration of FIG. 17. In this elastically deformed, aligned configuration, one or more sutures can be inserted into the device 200 through the aligned openings 215, 218, 220, as shown in FIG. 20. As shown in FIG. 21, once the sutures are positioned inside the device 200, the jaws 226, 228 can be opened, releasing their compressive force on the device 200, and allowing the device to elastically spring back toward its natural shape. In the example of FIGS. 20 and 21, the device 200 is used to secure two sutures 6 together to secure an annuloplasty ring 2 to a native mitral annulus 4. The sutures 6 can block the device 200 from returning completely to its natural shape, leaving a portion of the elastic deformation in the device such that the device is biased against the sutures. In the configuration of FIG. 21, the first and third sections 202, 206 exert a force toward the right on the suture 6, while the second section 204 exerts a force toward the left on the sutures, effectively pinching the sutures together with enough force to create sufficient frictional resistance to the sutures sliding longitudinally out of the device. Having three or more segments in the device 200 provides a more balanced force distribution on the sutures and enhances the device's grip in the sutures 6. The edges of each section 202, 204, 206 can also bite into the sutures 6 to some degree to enhance the device's grip on the sutures.

FIGS. 22-25 show another embodiment of a suture securement device 240 that functions in a manner similar to the device 200. The device 240 comprises three (or more) sections 242, 244, 246 coupled together by flexible spine segments 248, 250. Each section 242, 244, 246 comprises an annular wall that is open at one side opposite the spine. Compared to the segments 202, 204, 206 of the similar device 200, the segments 242, 244, 246 of the device 240 have a thicker annular wall and a narrower open region within the annular wall. This allows the device 240 to engage onto a suture with less twisting motion compared to the device 200. The first section 242 has an opening 252 in the annular wall and an inner suture engagement surface 258, the second section 244 has an opening 254 in the annular wall and an inner suture engagement surface 260, and the third section 246 has an opening 256 in the annular wall and an inner suture engagement surface 262.

In its natural state (not shown), the sections 242, 244, 246 of the device 240 are misaligned, like the device 200 in FIGS. 14-17. In the misaligned natural configuration, the end sections 242 and 246 are twisted about the spine 248, 250 in the direction of the surfaces 258 and 262 are facing, and the middle section 244 is twisted about the spine in the opposite direction. When the device 240 is elastically deformed to the position shown in FIG. 25 (such as with a tool similar to the tool 222), the openings 252, 254, 256 of the three sections are aligned, allowing a suture to be inserted laterally through the openings and into an axial passageway extending through the three sections 242, 242, 246.

With the suture positioned through the axial passageway, the device 240 can be released from compression and allowed to elastically return toward the natural position. Before reaching the natural position, the engagement surfaces 258, 260, 262 contact the suture and exert opposing lateral forces on the suture to hold the suture in the device 240 and prevent the suture from sliding longitudinally out of the device in either direction. Because the annular bodies of the sections 242, 244, 246 are thicker than those in the device 200, the engagement surfaces 258, 260, 262 contact the suture with less recoil motion compared to the device 200. This can allow for a stronger clamping force and more durability.

Some suture securement devices can have a generally curved shape. The embodiments shown in FIGS. 26-31 are examples of devices having a curved shape. In these embodiments, the device can have an upper major surface that is generally convex and a lower major surface that is generally concave. The upper and lower major surfaces can be substantially parallel to each other, with the devices having a substantially constant thickness between the two major surfaces. In some embodiments, the upper and lower major surfaces can be curved in one direction and non-curved in a perpendicular direction (like a sidewall of a cylinder), such that the surfaces have central axis of curvature. In some embodiments, both major surfaces can have a common central axis of curvature. In other embodiments, the major surfaces can be curved in other manners, such as having concentric spherical major surfaces that share a common center of curvature. By providing suture securement devices with a curved structure, the devices can be biased to provide greater resistance to sutures moving toward the concave direction while more readily allowing sutures to move toward the convex direction.

In some embodiments, such curved devices can be formed from a sidewall of a tube. The outer radius of the tube can define the curvature of the convex major surface of the device while the inner radius of the tube can define the curvature of the concave major surface of the device. The uniform thickness of a curved device can be equal to the wall thickness of the tube that the device is cut from. In other embodiments, the devices can be formed from a sidewall of a non-cylindrical tube, or from a wall of other three-dimensional objects having a curved wall, such as a hollow sphere, spheroid, ellipsoid, etc., or from other three-dimensional objects having a curvature.

Figure 26:
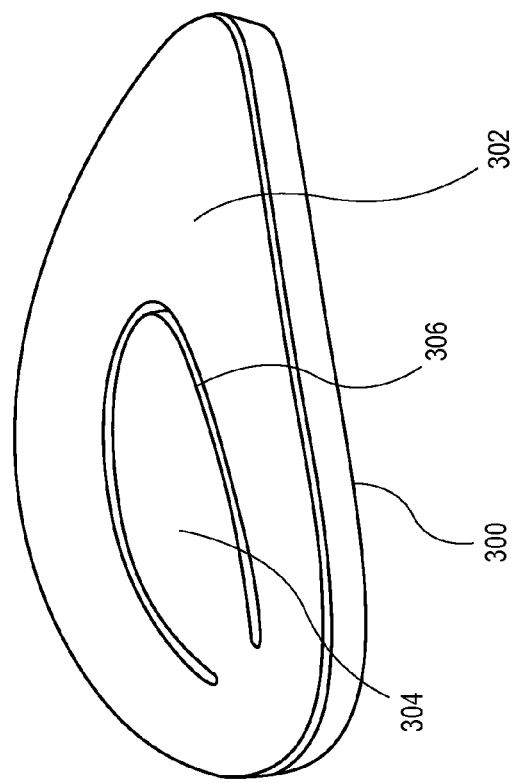

FIG. 26 shows an exemplary embodiment of a curved suture securement device 300. The device 300 comprises an annular outer body 302 and an inner body, or tab, 304 that is separated from the outer body by a "C" shaped slit 306. The convex, upper major surface of the device 300 is shown in FIG. 26. The tab 304 can have an elliptical shape and can extend from a connection to the outer body in the direction of the curvature of the device. One or more sutures can be inserted through the slit 306 from the concave, lower side of the device 300, causing the tab 304 to deflect upwardly. With sutures inserted through the slit 306, the biased tab 304 pinches the sutures and prevents them from sliding back through the slit toward the concave direction. Thus, the device 300 can be attached to sutures with the concave side of the device facing a prosthetic device or tissue from which the free ends of the sutures extend.

Figure 27:
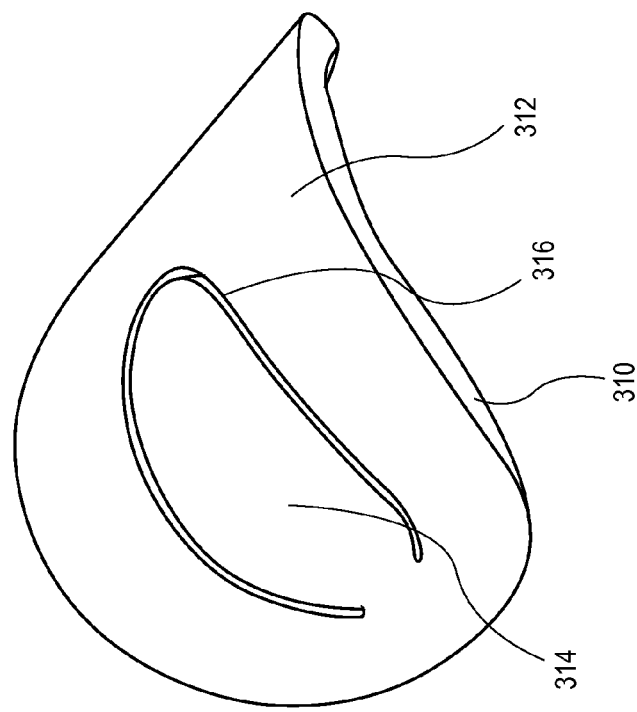
FIGS. 26-31 are perspective views of exemplary curved suture clips.

FIG. 27 shows an alternative embodiment of a curved suture securement device 310 that is similar to the device 300 but has greater curvature. The device 310 comprises an annular outer body 312, an inner tab 314, and a "C" shaped slit 316. The increased curvature of the device 310 relative to the device 300 can result in increased bias and increased resistance to sutures sliding through the slit 316 toward the concave direction. The embodiments 300 and 310 represent two examples of different curvatures, while other embodiments can have any other degree of curvature desired. Similarly, the thickness of the curved devices can vary and can be selected to provide a desired stiffness for the device.

Figure 28:
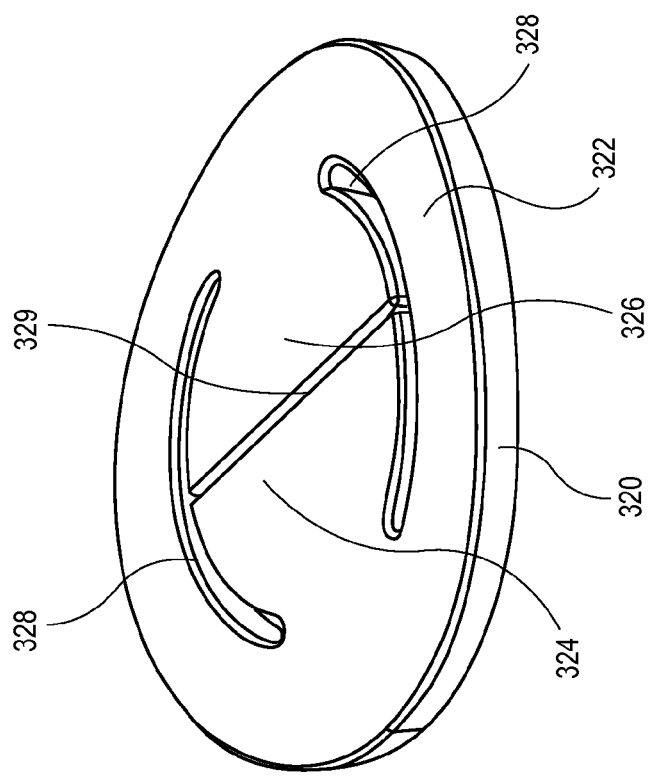

FIG. 28 shows an embodiment of a curved suture securement device 320 that comprises an annular outer body 322 and two opposing tabs 324, 326, similar to a flat version shown in FIGS. 11A-11C. The outer body 322 can have a generally circular shape and each of the tabs 324, 326 can have a generally half-circle shape. The tabs 324, 326 are separated from the outer body by two arcuate slots 328 and the tabs are separated from each other by a straight slit 329 that connects the two arcuate slots 328. One or more sutures can be inserted into the slit 329 from the lower convex side, deflecting both tabs 324, 326 upwardly in the direction of insertion. With the sutures inserted, the biased tabs allow the sutures to move upwardly in the convex direction with little resistance but prevent the sutures from moving downwardly in the concave direction.

Figure 29:
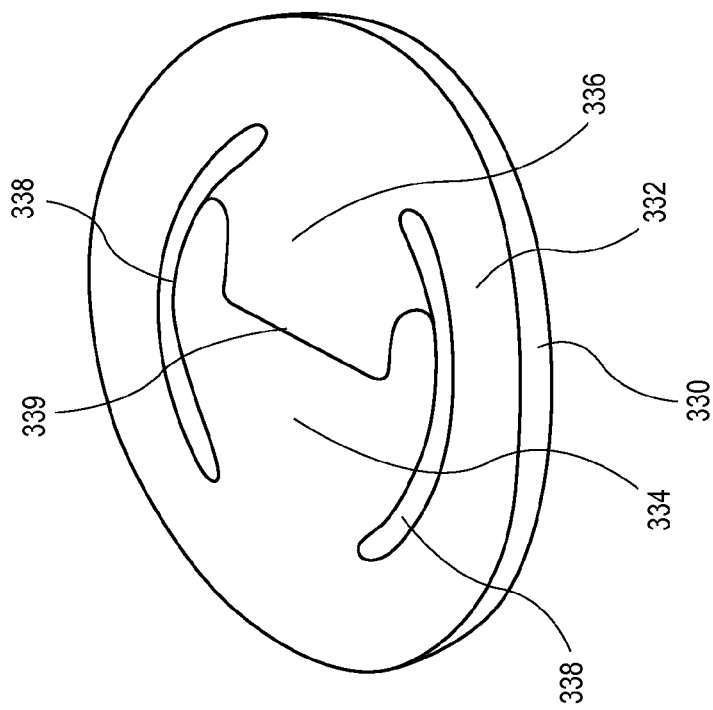

FIG. 29 shows another embodiment of a curved suture securement device 330 that comprises an annular outer body 332 and two opposing tabs 334, 336. The outer body 332 can have a generally circular shape and each of the tabs 334, 326 can extend inwardly from opposite ends of the outer body. The tabs 334, 336 are separated from the outer body by two arcuate slots 338 and the tabs are separated from each other by a slit 339 that connects the two arcuate slots 338. The slit 339 can have a straight middle portion for placement of sutures and angled or L-shaped end portions 331 at either end of the straight portion that can help retain the sutures in the straight portion of the slit 339 and prevent the sutures from migrating into the arcuate slots 338. The two tabs 334, 336 are thus dissimilar, with the larger left tab 334 extending around the right tab 336 on both sides at the L-shaped end portions 331 of the slit 339. One or more sutures can be inserted into the slit 339 from the lower convex side, deflecting both tabs 334, 336 upwardly in the direction of insertion. With the sutures inserted, the biased tabs allow the sutures to move upwardly in the convex direction with little resistance but prevent the sutures from moving downwardly in the concave direction.

Figure 30:
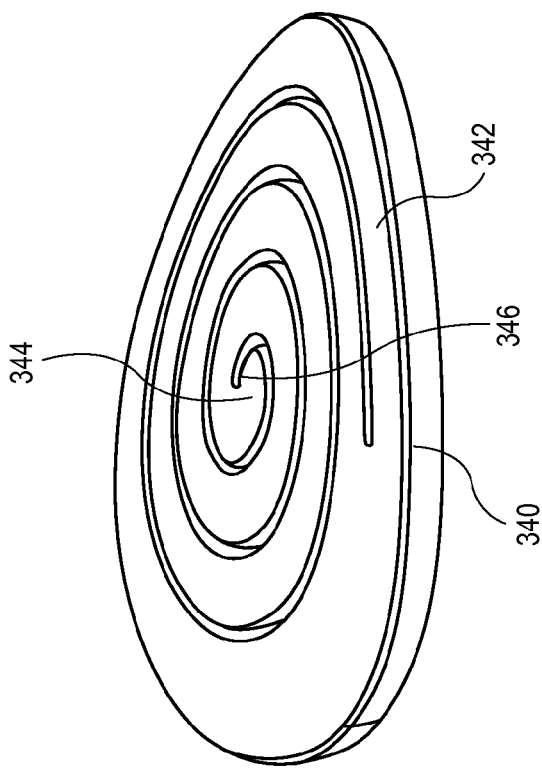

FIG. 30 shows an embodiment of a curved suture securement device 340 that comprises an annular outer body 342, a coiled or spiraled inner body 344 extending within the outer body, and a coiled or spiraled slit 346. Sutures can be inserted through the coiled slit 346 at any point along the slit, such as at the central end of the slit, from the concave side of the device, causing the coiled inner body to deform toward the convex side and causing a biased clamping force on the sutures that prevents the sutures from sliding back toward the concave direction.

Figure 31:
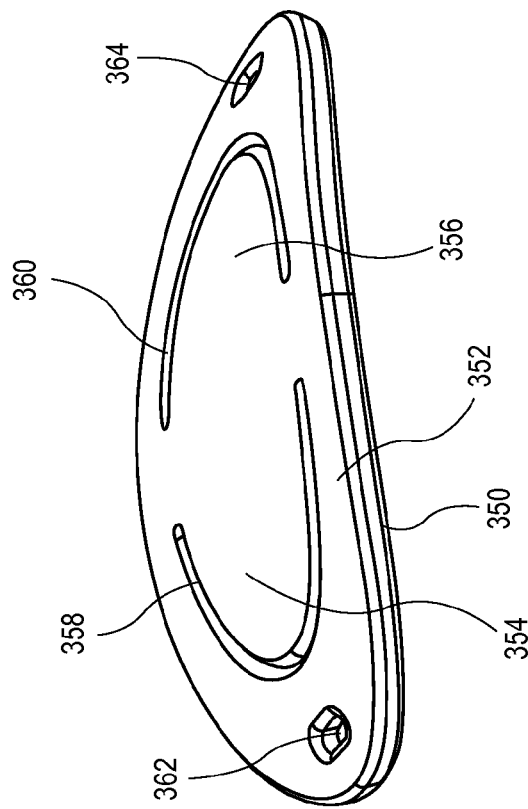

FIG. 31 shows an embodiment of a curved suture securement device 350 that comprises an annular outer body 352 and two inner tabs 354, 356 are defined within the outer body by two arcuate slits 358, 360, respectively. The tabs 354, 356 extend in opposite directions from a central portion of the device between the slits 358, 360. Each of the slits 358, 360 can receive one or more sutures from the concave lower side of the device, causing the respective tabs 354, 356 to deform upwardly and causing a biased clamping force on the sutures that prevents the sutures from sliding back toward the downward, concave direction.

In some embodiments, the device 350 can further comprise an opening 362 in one end of the outer body 352 adjacent the slit 358 and an opening 364 in an opposite end of the outer body 352 adjacent the slit 360. The openings 362 and 364 can be used to secure (e.g., suture) the device 350 to another surface, such as a surface of a prosthetic device or underlying tissue. Any of the suture clip embodiments disclosed herein can comprise additional openings, similar to the openings 362 and 364, for securing the clip to an underlying surface.

Any of the curved embodiments described herein can have a thickness of, for example, from about 0.001 inches to about 0.100 inches, such as about 0.010 inches. Any of the curved embodiments described herein can have a radius of curvature of the convex major surface of, for example, greater than about 2.0 mm, such as about 4.0 mm. Any of the curved embodiments described herein can comprise superelastic and/or shape memory material, such as Nitinol.

FIGS. 32-42 illustrate embodiments of suture clips that are initially formed in an in-plane configuration (e.g., a flat, in-plane configuration or a curved in-plane configuration) and are then are deformed and heat-set in an out-of-plane, functional configuration. As used with reference to FIGS. 32-42, the term "in-plane configuration" refers to the position of the tabs being generally in-plane with the outer body, and includes configurations such as those shown in FIGS. 26-31 having a curved or arched overall shape.

The clip embodiment 400 shown in FIGS. 32-35 comprises an annular outer body 402 and two opposing tabs 404, 406 that are separated from the outer body by slots 408. The clip 400 is initially formed in a flat, planar configuration with the two tabs 404, 406 being in-plane with the outer body 402. The clip 400 can be cut from a flat sheet of material, for example. The initial flat, in-plane clip can have a circular shape. The flat, circular clip 400 can then be deformed to the configuration shown in FIGS. 32-35 by applying compression at the edges adjacent to the ends labeled 420 in the directions of arrows 421 while pushing the tabs 404, 406 upward out-of-plane from the outer body. The compression at the ends 420 causes the annular body 402 to become elliptical and causes the tabs 404, 406 to move toward each other and interlock in the out-of-plane formation, with the arms 410 of the tab 404 engaged with the shoulders 416 of the tab 406 and the end portion 414 of the tab 406 engaged with the intermediate portion 412 of the tab 404.

The clip 400 can be comprised of a superelastic and/or shape memory material, such as Nitinol, such that the clip 400 can be heat-set in the deformed configuration shown in FIGS. 32-35. In order to hold the clip 400 in the deformed configuration shown in FIGS. 32-35 during a heat-setting process, the upper surface of the annular body 402 can be held against a flat, planar surface (as illustrated by the dashed line in FIG. 35) while the tabs 404, 406 are bent into the interlocked configuration through an opening in the flat, planar surface. For example, a flat plate with a hole in it can be used as the flat, planar surface. While the clip 400 is held against such a plate with the tabs extending through the hole in the interlocked configuration, the temperature of the clip material can be increased to a sufficient level for a sufficient time to allow the Nitinol to become heat-set in the configuration illustrated. The heat-setting process can comprise, for example, placing the deformed clip in a furnace to heat the clip above a given temperature for a given period of time, and then immersing the heated clip into a cooler body of water to quench the clip below a certain temperature and complete the heat-setting process.

The deflection of the tabs 404, 406 twists the annular body 402 at each of the end portions 420, causing those end portions 420 to deflect downward, as shown in FIGS. 34 and 35. With the tabs 404, 406 interlocked, one or more sutures of any diameter can be inserted through the interface 418 between the two tabs to bend the tabs further upward and create a biased locking mechanism that resists movement of the sutures in the downward direction. The arms 410 can also block the sutures from sliding laterally out of the interface 418.

FIGS. 36-38 illustrate a suture clip embodiment 430 that is similar to the embodiment 400. The clip 430 comprises an annular outer body 432 and two tabs 434, 436 that interlock in an out-of-plane configuration to create a biased suture engagement similar to the tabs 404, 406 of the clip 400. The clip 430 can be initially formed in a curved, in-plane, circular configuration, like the embodiment 330 shown in FIG. 29. The annular body 432 can be held against a concave surface (as illustrated by the dashed line in FIG. 38), such as a curved plate, with the end portions 450 compressed together in the direction of arrows 451 and the tabs 434, 436 deflected upward, such as through a hole in the plate, and in the interlocking position shown in FIG. 37. The clip 430 can be heat-set in this configuration, as described above, such that the annular body 432 is arched with downwardly deflected end portions 450, the arms 440 of the tab 434 are engaged on the shoulder portions 446 of the tab 436, and the end portion 444 of the tab 436 engaged with the intermediate portion 442 of the tab 434. With the tabs 434, 436 interlocked, one or more sutures of any diameter can be inserted through the interface 448 to bend the tabs further upward and create a biased locking mechanism that resists movement of the sutures in the downward direction. The arms 440 can also block the sutures from sliding laterally out of the interface 448.

FIGS. 39-42 illustrate another embodiment of a suture clip 460 that is initially formed with an elongated, elliptical annular outer body 462 instead of a circular outer body, as with the clips 400 and 430. By initially forming the clip 460 in an elongated, elliptical shape, as shown in FIG. 39, the clip 460 can be deformed into a generally circular shape, as shown in FIG. 40, by compressing diametrically opposing edges 480 in the direction of arrows 482. The embodiments 400, 430 and 460 illustrate that a suture clip can be designed to result in any desirable shape after a heat-setting process by selecting a corresponding initial configuration. In other embodiments, the annular outer body can have a polygonal shape or other non-elliptical, non-circular shape. In the embodiment 460, the tabs 464, 466 are slightly longer than the tabs 434, 436 of the clip 430, but otherwise function in a similar manner such that they have an interlocked configuration after the heat-setting process with the arms 470 engaged with the shoulders 476 and the end portion 474 engaged with the intermediate portion 472. With the tabs 464, 466 interlocked, one or more sutures of any diameter can be inserted through the interface 478 to bend the tabs further upward and create a biased locking mechanism that resists movement of the sutures in the downward direction. The arms 470 can also block the sutures from sliding laterally out of the interface 478.

In the embodiments 400, 430 and 460, the opposing tabs may not interlock together in a deformed, out-of-plane configuration unless the annular outer body is compressed together to allow the opposing tabs to move closer together. Without the compression of the outer body, a gap is formed between the ends of the two tabs when they are bent out-of-plane from the outer body and gaps are formed between the arms of the one tab and the shoulders of the other tab. These gaps may not allow the two tabs to properly interlock in the deformed position. Thus, by compressing the annular body together, and heat-setting the clip in the compressed state, the tabs are provided with the ability to engage each other in the interlocked configuration. The touching interface between the end portions of the tabs allows the tabs to exert a clamping force on any diameter of sutures, even very small diameter sutures.

Figure 43:
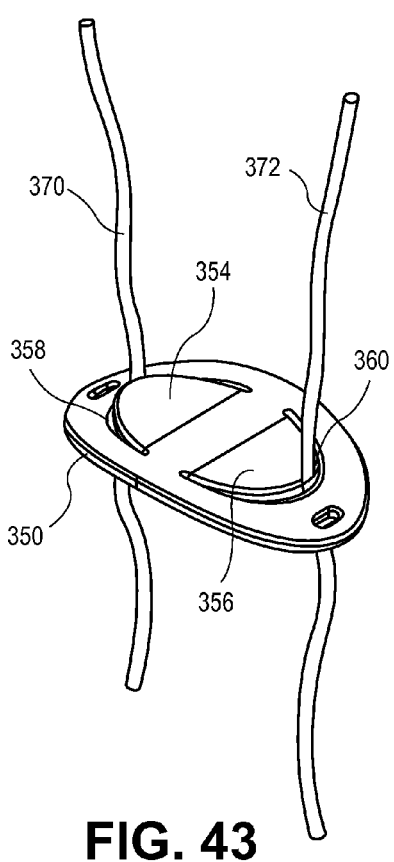
FIGS. 43-45 show different way in which sutures can be used with the clip of FIG. 31.
Figure 44:
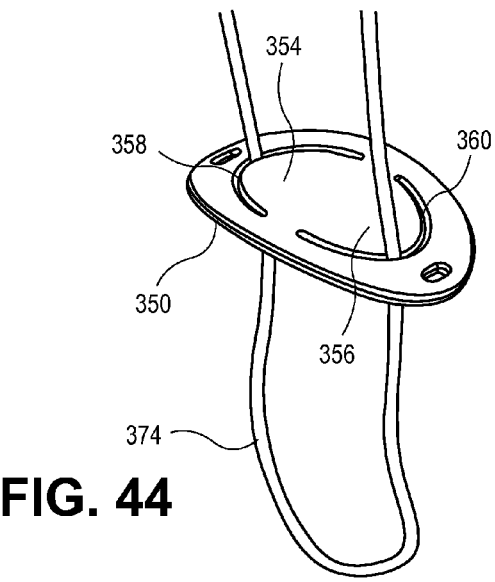
Figure 45:
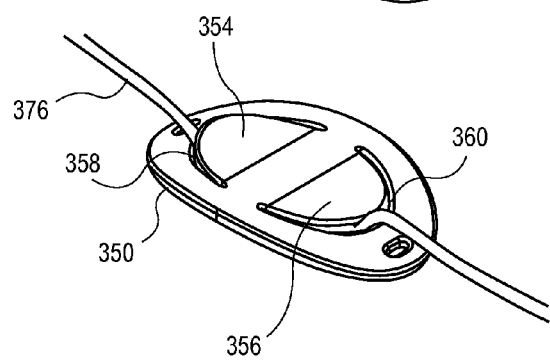

FIGS. 43-44 show various configurations in which the clip 350 of FIG. 31 can be engaged with sutures. As shown in FIG. 43, the clip 350 can be used to secure two different sutures. The suture 370 is engaged in the slit 358 and the suture 372 is engaged in the opposite slit 360. Due to the curvature of the clip 350 and the upward deflection of the tabs 354, 356, the sutures 370, 372 are allowed to move upwardly through the slits 358, 360, but are prevented from sliding downwardly through the slits. As shown in FIG. 44, the clip 350 can also be used to secure two different portions of the same suture 374 that both pass upwardly through opposite slits. The two free ends of the suture 374 can be pulled upwardly to tighten the lower looped portion of the suture toward the bottom of the clip, but the tabs 354, 356 prevent the suture from sliding downward and loosening. FIG. 45 shows another variation where a single suture 376 passes through both slits 358, 360. In FIG. 45, the suture 376 has free ends that extend in opposite lateral directions from the slits, rather that extending upwardly as in FIG. 44.

Figure 47:
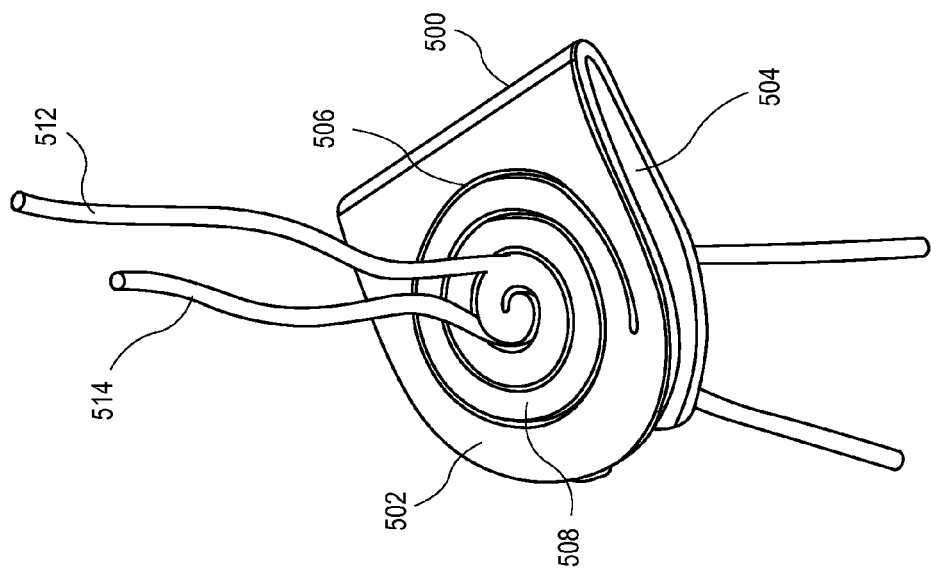
FIGS. 46 and 47 are views of another exemplary suture clip.
Figure 46:
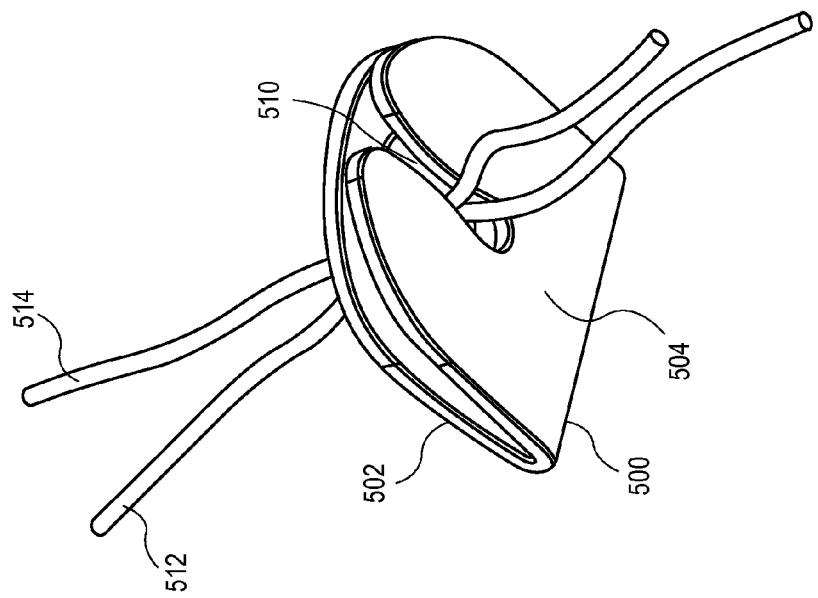

FIGS. 46 and 47 show an embodiment of a suture clip 500 that comprises two folded panels 502 and 504. The upper panel 502 is similar to the clip 340 in FIG. 30, in that it comprises a spiral slit 506 that defines a spiral tab 508. The lower panel 504 comprises a slot 510 extending from one end to the center of the lower panel. The upper and lower panels 502 and 504 can be coupled together along a fold at one end opposite the slot 510. One or more sutures 512, 514 can be threaded through the spiral slit 506 in the upper panel and through the slot 510 in the lower panel to secure the sutures. The upper panel 502 can be curved, like the clip 340 in FIG. 30, such that the spiral tab 508 is biased to allow the sutures to slide upwardly through the slit 506 but prevents the sutures from sliding downwardly toward the lower panel 504. The slot 510 can help prevent the sutures 512, 514 from migrating around the spiral slit 506, keeping the sutures near the center of the spiral.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

In view of the many possible embodiments to which the principles of this disclosure may be applied, it should be recognized that the illustrated embodiments are only preferred examples and should not be taken as limiting the scope of the disclosure.

We claim:
1. A device for securing one or more sutures, comprising:
a generally disk-shaped body having an annular outer body that defines an annular outer edge, a first tab extending radially inwardly from a first side of the annular outer body and a second tab extending radially inwardly from a second side of the annular outer body;
first and second curved slots passing through the disk-shaped body within the annular outer body, wherein the first and second curved slots define sides of the first and second tabs; and
a middle slit connecting the curved slots and separating the first and second tabs, the slit and curved slots generally forming a closed H-shaped opening through the body within the annular outer body, the slit being sized to receive and hold one or more sutures, and opposed edges of the first and second tabs positioned across the slit from each other form suture engagement portions;
wherein each of the first and second tabs has a base end that connects to the annular outer body and a free end that borders the slit, the base ends having a width that extends between an end of the first curved slot and an opposing end of the second curved slot, and the widths of the base ends of the first and second tabs are shorter than widths of the free ends of the first and second tabs, such that the first and second tabs are encouraged to articulate relative to the annular outer body along the width of their base ends;
wherein the device comprises an elastically resilient material and has a flat natural configuration when no sutures are positioned in the slit;
wherein the device has an active configuration wherein the first and second tabs are elastically deformed out of a plane defined by the annular outer body when one or more sutures are positioned through the slit in a direction generally perpendicular to the plane defined the annular outer body;
wherein the elastically deformable first and second tabs allow the device to change from the natural configuration to the active configuration to receive and secure one or more sutures between the suture engagement portions; and
wherein, in the active configuration, the suture engagement portions exert a pinching force on the one or more sutures that restricts the sutures from sliding through the slit in at least one longitudinal direction of the sutures.

2. The device of claim 1, wherein the device has a substantially uniform thickness in the natural configuration.

3. The device of claim 1, wherein the slit has a straight suture receiving portion and first and second angled end portions on opposite ends of the suture receiving portion configured to block received sutures from sliding laterally along the slit from the suture receiving portion of the slit into the curved slots, wherein the first angled end portion of the slit is adjacent to the first curved slot and the second angled end portion of the slit is adjacent to the second curved slot.

4. The device of claim 1, wherein the slit has a straight suture receiving portion and first and second serpentine end portions on opposite sides of the suture receiving portion configured to block received sutures from sliding laterally along the slit from the suture receiving portion into the curved slots, wherein the first serpentine end portion of the slit is adjacent to the first curved slot and the second serpentine end portion of the slit is adjacent to the second curved slot.

5. The device of claim 1, wherein the curved slots terminate in enlarged circular portions located where the first and second tabs join with the annular outer body, such that the enlarged circular portions reduce stress concentrations when the tabs elastically deform out of the plane defined by the annular outer body.

6. The device of claim 1, wherein the tabs are equal in size.

7. The device of claim 1, wherein the tabs are dissimilar, with one being larger than the other.

8. The device of claim 1, wherein elastic deformation of the first and second tabs occurs at locations where the first and second tabs join with the annular outer body.

9. The device of claim 1, wherein the curved slots have curved radially inner surfaces, the curved radially inner surfaces being curved lateral surfaces of the first and second tabs.

10. The device of claim 1, wherein each of the curved slots has a constant width along a majority of the length of the respective curved slot.

11. The device of claim 1, wherein the annular outer body comprises two opposing radial cutouts in the outer edge of the device.

12. The device of claim 1, wherein the slit extends a distance between the first and second tabs that is at least 50% of an outer diameter of the device.

13. The device of claim 1, wherein each of the first and second tabs has a length dimension that extends from the slit to the annular outer body in a direction perpendicular to the slit, wherein the annular outer body has a radial dimension that extends from the curved slot radially outwardly to the annular outer edge, and wherein the length dimension of the first and second tabs is greater than or equal to the radial dimension of the annular outer body.

14. The device of claim 1, further comprising a suture extending through the device between the first and second tabs, wherein the first and second tabs are bent relative to the annular outer body at junctions where the first and second tabs are connected to the annular outer body.

15. A method of using the device of claim 1, comprising inserting a suture through the device between the first and second tabs, the insertion of the suture occurring while the first and second tabs are bent relative to the annular outer body at junctions where the first and second tabs are connected to the annular outer body.

16. A device for securing one or more sutures, comprising:
a generally disk-shaped body having an annular outer body that defines an annular outer edge; a first tab extending radially inwardly from a first side of the annular outer body and a second tab extending radially inwardly from a second side of the annular outer body;
first and second slots passing through the disk-shaped body within the annular outer body, wherein the first and second slots define lateral sides of the first and second tabs; and
a middle slit connecting the first and second slots and separating the first and second tabs, the slit and two slots forming a closed opening through the body within the annular outer body, the slit being configured to receive and hold at least one suture such that opposed edges of the first and second tabs positioned across the slit from each other form suture engagement portions;
wherein the slit comprises a straight suture receiving portion having a first end closer to the first slot and a second end closer to the second slot, and the slit further comprises first and second non-straight portions on opposite ends of the straight suture receiving portion with the first non-straight portion extending from the first end of the straight suture receiving portion toward the first slot and the second non-straight portion extending from the second end of the straight suture receiving portion toward the second slot, the non-straight portions of the slit being configured to block a received suture from sliding laterally along the slit from the suture receiving portion into either of the slots;

wherein the device comprises an elastically resilient material and has a natural configuration when no suture is positioned in the slit;

wherein the device has an active configuration wherein the first and second tabs are elastically deformed when at least one suture is positioned through the slit; and wherein, in the active configuration, the suture engagement portions exert a pinching force on at least one suture extending through the slit that restricts the at least one suture from sliding through the slit in at least one longitudinal direction of the suture.

17. The device of claim 16, wherein:
the slit extends in a first major direction of the device that is perpendicular to the longitudinal direction of a suture passing through the slit, and the first and second tabs extend toward each other in a second major direction of the device that is perpendicular to the first major direction and perpendicular to the longitudinal direction of a suture passing through the slit; and the first and second non-straight portions of the of the slit extend back and forth in the second major direction as the slit extends radially outwardly in the first major direction.

18. The device of claim 17, wherein the first and second non-straight portions of the of the slit comprise serpentine sections of the slit that curve back and forth in the second major direction as the slit extends radially outwardly in the first major direction.

19. The device of claim 16, wherein the slit extends a distance across the device that is at least 50% of an outer diameter of the device.

20. The device of claim 16, wherein the first and second slots have a constant radial width along a majority of the length of the respective slot.

21. The device of claim 16, wherein the largest diameter of the device is less than 5 mm.

22. A device for securing one or more sutures, comprising:

a generally disk-shaped body having a thickness and a radial dimension perpendicular to the thickness, the body having an annular outer body that defines an annular outer radial edge; a first tab extending radially inwardly from a first side of the annular outer body and a second tab extending radially inwardly from a second side of the annular outer body;

first and second slots passing through the thickness of the disk-shaped body and positioned radially within the annular outer body, wherein the first and second slots define lateral sides of the first and second tabs; and a middle slit extending through the thickness of the body and radially connecting the first and second slots and separating the first and second tabs, the slit and two slots forming a closed opening passing through the thickness of the body and positioned radially within the annular outer body, the slit being configured to receive and hold at least one suture such that opposed surfaces of the first and second tabs positioned across the slit from each other form suture engagement portions, and wherein the slit has a constant spacing width between the first and second tabs across the thickness of the body;

wherein the device comprises an elastically resilient material and has a natural configuration when no suture is positioned in the slit;

wherein the device has an active configuration wherein the first and second tabs are elastically deformed when at least one suture is positioned through the slit; and wherein, in the active configuration, the suture engagement portions exert a pinching force on at least one suture extending through the slit that restricts the at least one suture from sliding through the slit in at least one longitudinal direction of the suture.

23. The device of claim 22, wherein the slit comprises a straight suture receiving portion having a first end closer to the first slot and a second end closer to the second slot, and the slit further comprises first and second non-straight portions on opposite ends of the straight suture receiving portion with the first non-straight portion extending from the first end of the straight suture receiving portion toward the first slot and the second non-straight portion extending from the second end of the straight suture receiving portion toward the second slot, the non-straight portions of the slit being configured to restrict a received suture from sliding radially along the slit from the suture receiving portion into either of the slots.

* * * * *